United States Patent [19]
Cheng et al.

[11] Patent Number: 5,192,764
[45] Date of Patent: Mar. 9, 1993

[54] PYRAZINONE N-OXIDE NUCLEOSIDES AND ANALOGS THEREOF

[75] Inventors: Yung-Chi Cheng, Woodbridge; Tai-Shun Lin, North Haven, both of Conn.; Thomas J. Bardos, Snyder, N.Y.

[73] Assignees: Research Foundation of State of N.Y., Albany, N.Y.; Yale University, New Haven, Conn.

[21] Appl. No.: 707,536

[22] Filed: May 30, 1991

[51] Int. Cl.⁵ .................. A61K 31/495; C07D 241/02
[52] U.S. Cl. .................................. 514/252; 514/255; 544/405; 544/408
[58] Field of Search ................ 544/408, 405; 514/252, 514/255

[56] References Cited

U.S. PATENT DOCUMENTS

| | | | |
|---|---|---|---|
| 4,868,187 | 9/1989 | Ogilvie | 544/317 |
| 4,900,828 | 2/1990 | Belica et al. | 544/317 |
| 5,041,449 | 8/1991 | Belleau et al. | 544/317 |
| 5,043,339 | 8/1991 | Beauchamp | 544/317 |

FOREIGN PATENT DOCUMENTS

| | | | |
|---|---|---|---|
| 167385 | 1/1986 | European Pat. Off. | 544/317 |
| 311100 | 4/1989 | European Pat. Off. | 544/317 |

OTHER PUBLICATIONS

Neenan and Rohde, *J. Med. Chem.*, 16, 580 (1973).
Cheng, et al., *Ann. NY Acad. Sci.*, 255, 352 (1975).
Cheng, et al., *Antimicrobial Agents and Chemo.*, 10, 119 (1976).
Kotick, et al., *Jour. Org. Chem.*, 34, 3806 (1969).
Bobek, et al., *J. Med. Chem.*, 20, 458 (1977).
Berkowitz, et al., *J. Med. Chem.*, 16, 183 (1973).
Bobek and Bloch, *J. Med. Chem.*, 15, 164 (1972).
Ryu and Bardos, *J. Heterocyclic Chem.*, 16, 1049 (1979).
Kulikowski and Shugar, *J. Med. Chem.*, 17, 269 (1974).
De Clercq and Shugar, *Biochem. Pharmacol.*, 24, 1073 (1975).
De Clercq, et al., *Antimicrob. Agents and Chemo.*, 13, 545 (1978).
De Clercq et al., *Pure and Appl. Chem.*, 55, 623 (1983).
Bernaerts and De Clercq, *Nucleosides and Nucleotides*, 6, 421 (1987).
Swierkowski and Shugar, *J. Med. Chem.*, 12, 533 (1969).
Efange, et al., *J. Med. Chem.*, 28, 904 (1985).
Greengrass, et al., *J. Med. Chem.*, 32, 618 (1989).
Okabe, et al., *J. Org. Chem.*, 53, 4780 (1988).
Chen, et al., *J. Med. Chem.*, 33, 1555 (1990).
Reichmann et al., *Carbohydrate Res.*, 42, 233 (1975).
Su, et al., *J. Org. Chem.*, 46, 1790 (1981).
Borthwick, et al., *J. Med. Chem.*, 33, 179 (1990).
Mansuri, et al., *Tet. Letters*, 32, 1287 (1991).
Watanabe, et al., *J. Med. Chem.*, 26, 152 (1983).
Niedzwicki, et al., *Biochem. Pharmacol.*, 31, 1857 (1982).
Lin, et al., *Nucleosides and Nucleotides*, 9 559 (1990).
Karmas and Spoerri, *J. Amer. Chem. Soc.*, 74, 1580 (1952).
Tanaka, et al., *J. Med. Chem.*, 34, 1508 (1991).
Tanaka, et al., *J. Med. Chem.*, 34, 1394 (1991).
Efange, et al., *Nucleosides and Nucleotides*, 4, 545 (1985).
Lewandowski, et al., *Antimicrob. Agents and Chemo.*, 33, 340 (1989).
De Clercq, et al., *J. Med. Chem.*, 26, 661 (1983).
Lin and Prusoff, *J. Med. Chem.*, 21, 109 (1978).
Watanabe, et al., *J. Med. Chem.*, 22, 21 (1979).
Lin, et al., *J. Med. Chem.*, 30, 440 (1987).

(List continued on next page.)

*Primary Examiner*—Cecilia Tsang
*Attorney, Agent, or Firm*—Henry D. Gleman; R. Neil Sudol

[57] ABSTRACT

This invention relates to nucleoside and acyclo analogs containing 5- or 6-substituted 2-pyrazinone-4-N-oxide. These compounds are useful for treating various conditions including viral infections, cancer, fungal infections, bacterial infections, microbial infections and related disease states. This invention also relates to pharmaceutical formulations containing these compounds. In addition, this invention relates to methods of treating the above-described conditions in animals and in particular, humans.

46 Claims, 17 Drawing Sheets

OTHER PUBLICATIONS

Kim, et al., *J. Med. Chem.*, 30, 862 (1987).
Bamford, et al., *J. Med. Chem.*, 33, 2488 (1990).
Bamford, et al., *J. Med. Chem.*, 33, 2494 (1990).
Jones, et al., *Tet. Letters*, 45, 4415 (1979).
Fox, et al., *Antiviral Chemo*, 219 (1981).
Fleet, et al., *Tetrahedron*, 44, 625 (1988).
De Clercq, et al., *Mol. Pharmacol.*, 14, 422 (1978).
Torrence and Bhooshan, *J. Med. Chem.*, 20, 974 (1977).
Baba, et al., *Biochem. Biophys. Res. Comm.*, 142, 128 (1987).
Chu, et al., *Tet. Letters*, 29, 5349 (1988).
Gupta, et al., *J. Med. Chem.*, 18, 973 (1975).
Hardi, et al., *Antimicrobial Agents and Chemo.*, 10, 682 (1976).
Schroeder, et al., *J. Med. Chem.*, 24, 109 (1981).
Heidelberger and Boohar, *Biochem Biophys. Acta*, 91, 639 (1964).
Dale et al., *Biochemistry*, 14, 2447 (1975).
Mertes and Saheb, *J. Pharm. Sci.*, 52, 508 (1963).
Danenberg and Heidelberger, *J. Med. Chem.*, 16, 712 (1973).
Arai and Daves, Jr., *J. Heterocyclic Chem.*, 15, 351 (1978).
Dieck and Heck, *Jour. Amer. Chem. Soc.*, 96, 1134 (1974).
Hough and Otter, *Chem. Comm.*, 6, 173 (1966).
Fox et al., *Jour. Amer. Chem. Soc.*, 83, 4066 (1966).
Scheit, *Chem. Ber.*, 99, 3884 (1966).
Ritzmann, et al., *Carbohydrate Res.*, 39, 227 (1975).
Dyatkina and Azhayev, *Synthesis*, 961 (1984).
Bardos and Kalman, *J. Pharm. Sci.*, 55, 606 (1966).
Kaufman and Heidelberger, *Science*, 145, 585 (1964).
Richman, et al., *New Engl. Jour. Med.*, 317, 192 (1987).
Mitsuya, et al., *Proc. Natl. Acad. Sci. USA*, 82, 7096 (1985).
Mitsuya and Broder, *Proc. Natl. Acad. Sci. USA*, 83, 1911 (1986).
Balzarini et al., *Mol. Pharmacol.*, 32, 162 (1987).
Lin et al., *Bioch. Pharmacol.*, 36, 311 (1987).
Mitsuya et al., *Science*, 226, 172 (1984).
Graham and Whitmore, *Cancer Research*, 30 2636 (1970).
Barre-Sinoussi, et al., *Science*, 220, 868 (1983).
Shugar, *FEBS Lett.*, 40, S48 (1974).
Rabson, *Federation Proc.*, Part I, 31, 1625 (1974).
Davis, et al., *J. Virology*, 13, 140 (1974).
Schaeffer, et al., *Nature*, 272, 583 (1978).
Elion, et al., *Proc. Natl. Acad. Sci. USA*, 74, 5716 (1977).
De Clercq et al., *Proc. Natl. Acad. Sci. USA*, 76, 2947 (1979).
Allaudeen et al., *Proc. Natl. Acad. Sci. USA*, 78, 2698 (1981).
Robins, et al., *Adv. Enzyme Regul.*, 24,29, (1986).
Gilbert and Knight, *Antimcrob. Agents and Chemo.*, 30, 201 (1986).
Davis, et al., *J. Virol.*, 26, 603 (1978).
Remis, *Antibiotics Chemother.*, 27, 164 (1980).
Rapp and Vanderslice, *Virology*, 22, 321 (1964).
Rawls, et al., *Proc. Soc. Exp. Biol. Med.*, 115, 123 (1964).
Prusoff and Ward, *Biochem. Pharmacol.*, 25, 1233 (1976).
Salzman, *Virology*, 10, 150 (1960).
Nemes and Hilleman, *Proc. Soc. Exp. Biol. Med.*, 119, 515 (1965).
Yung-Chi Cheng, *Biochem. Biophys. Acta*, 452, 370 (1976).
Stellwagen and Tomkins, *Proc. Natl. Acad. Sci. USA*, 68, 1147 (1971).
Stellwagen and Tomkins, *J. Mol. Biol.*, 56, 167 (1971).
Chen, et al., *J. Biol. Chem.*, 251, 4833 (1976).
Vazquez-Padua, et al., *Cancer Comm.*, 2, 55, (1990).
Foster, et al., *J. Biol. Chem.*, 266, 238 (1991).

FIGURE 1 - SCHEME I
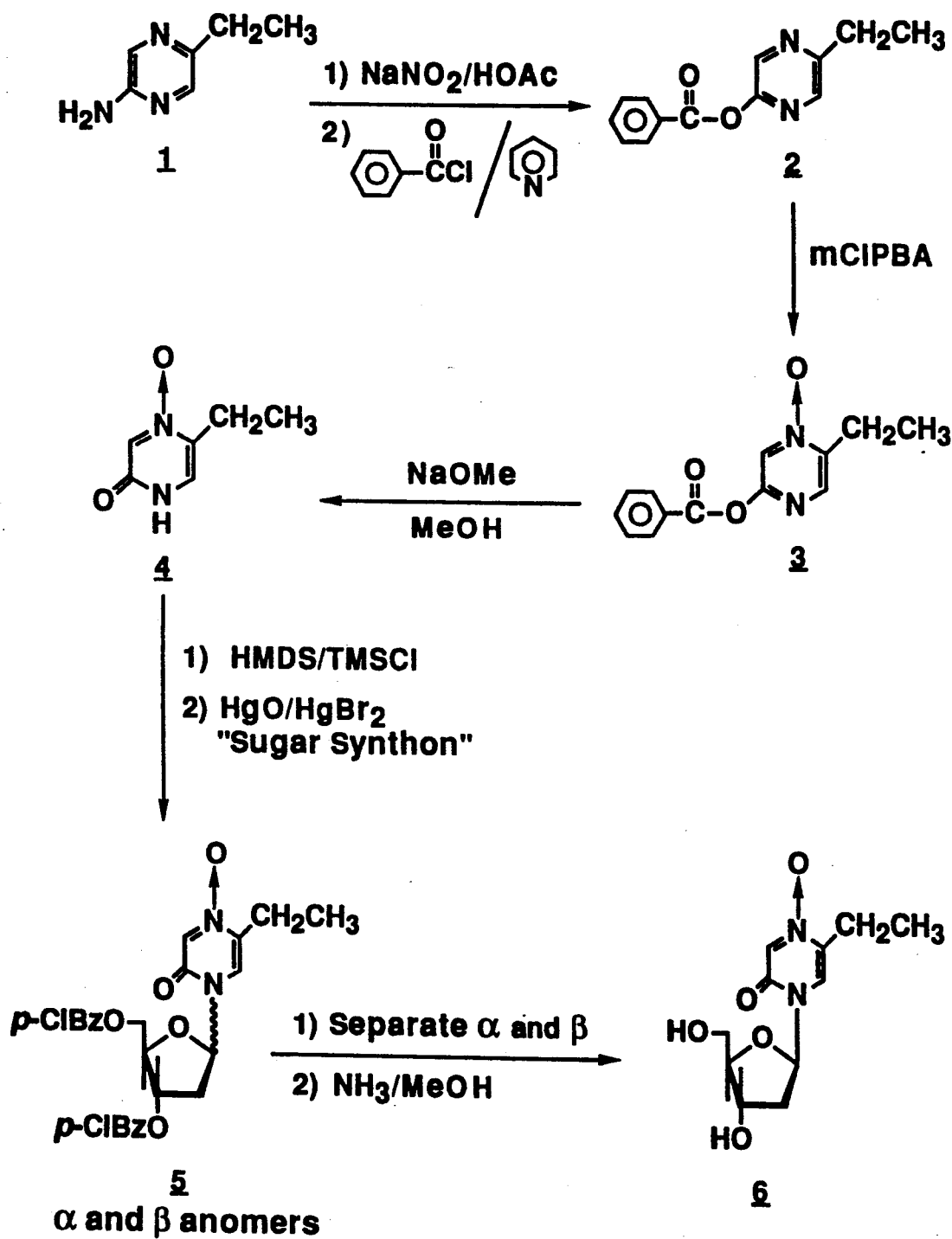

FIGURE 2 - SCHEME II
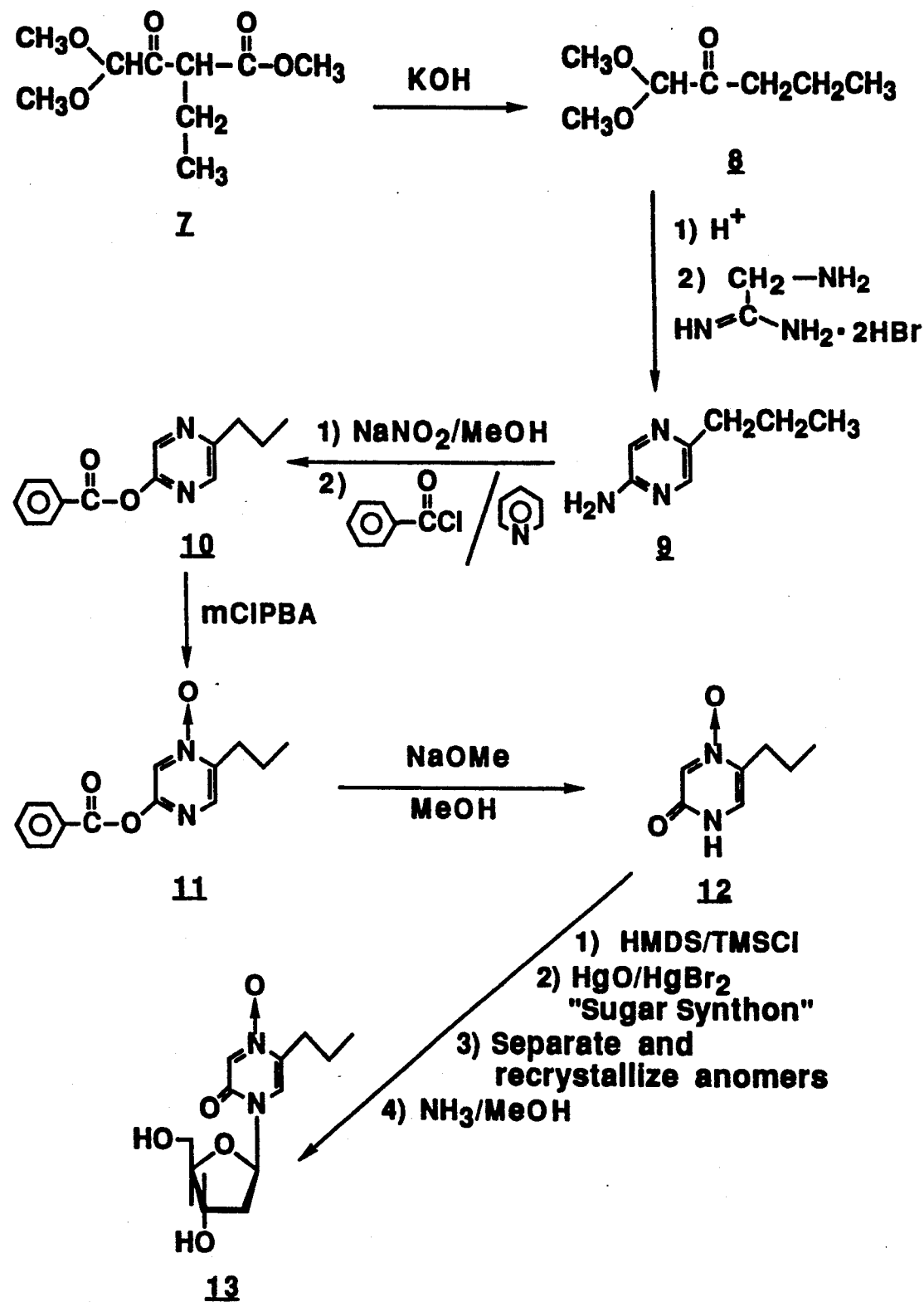

FIGURE 3 - SCHEME III
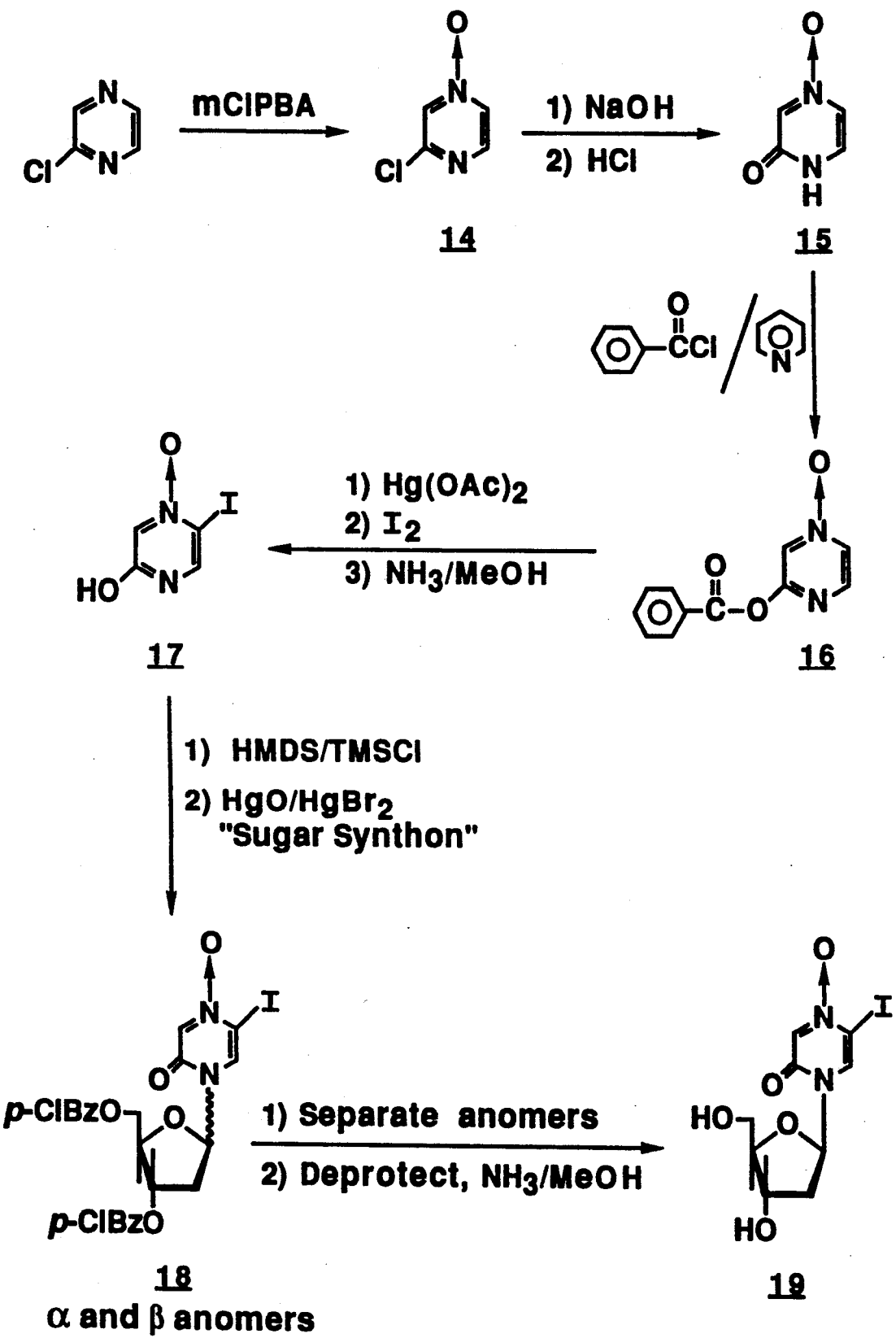

FIGURE 4 - SCHEME IV
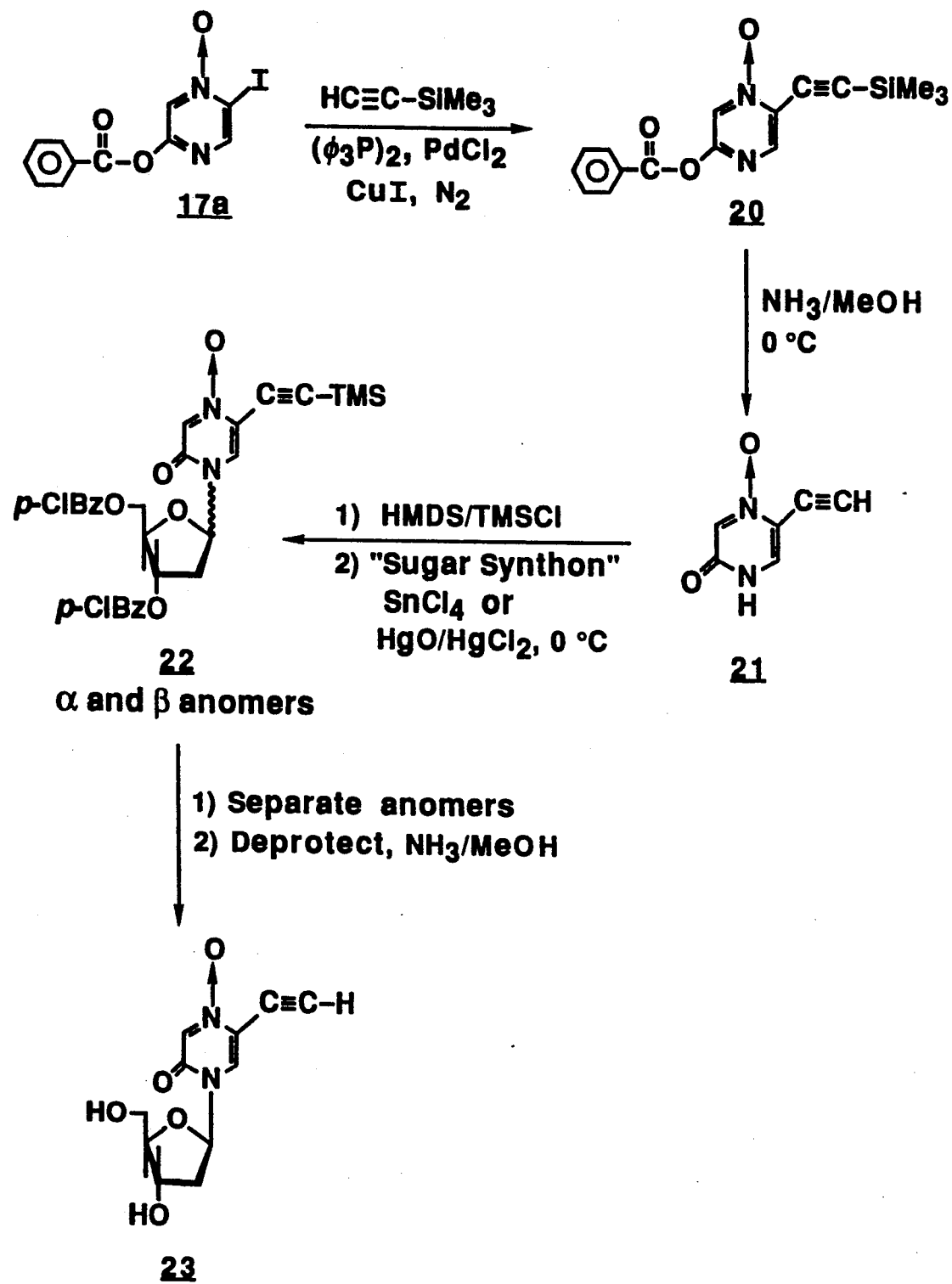

FIGURE 5 - SCHEME V
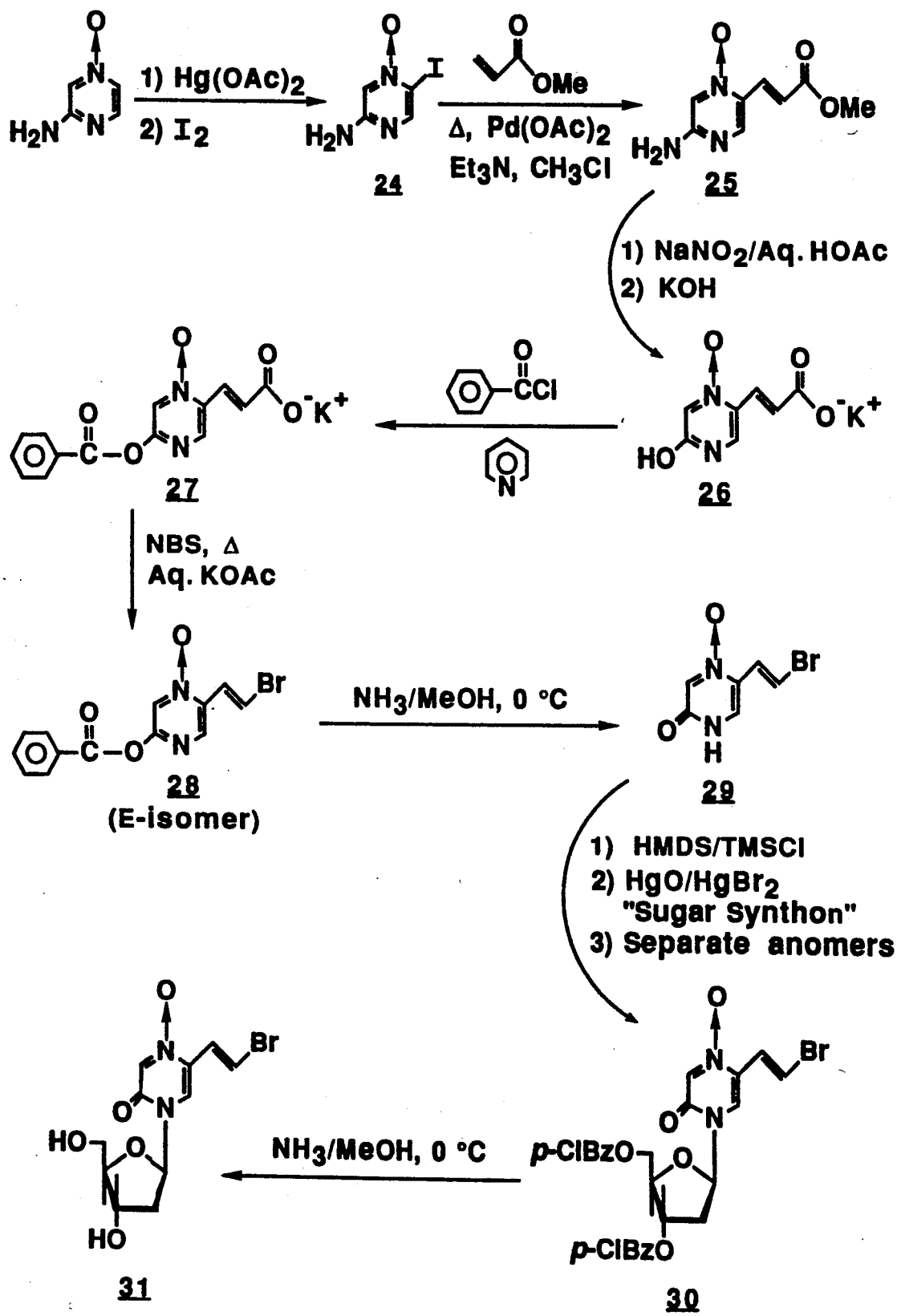

FIGURE 6 - SCHEME VI
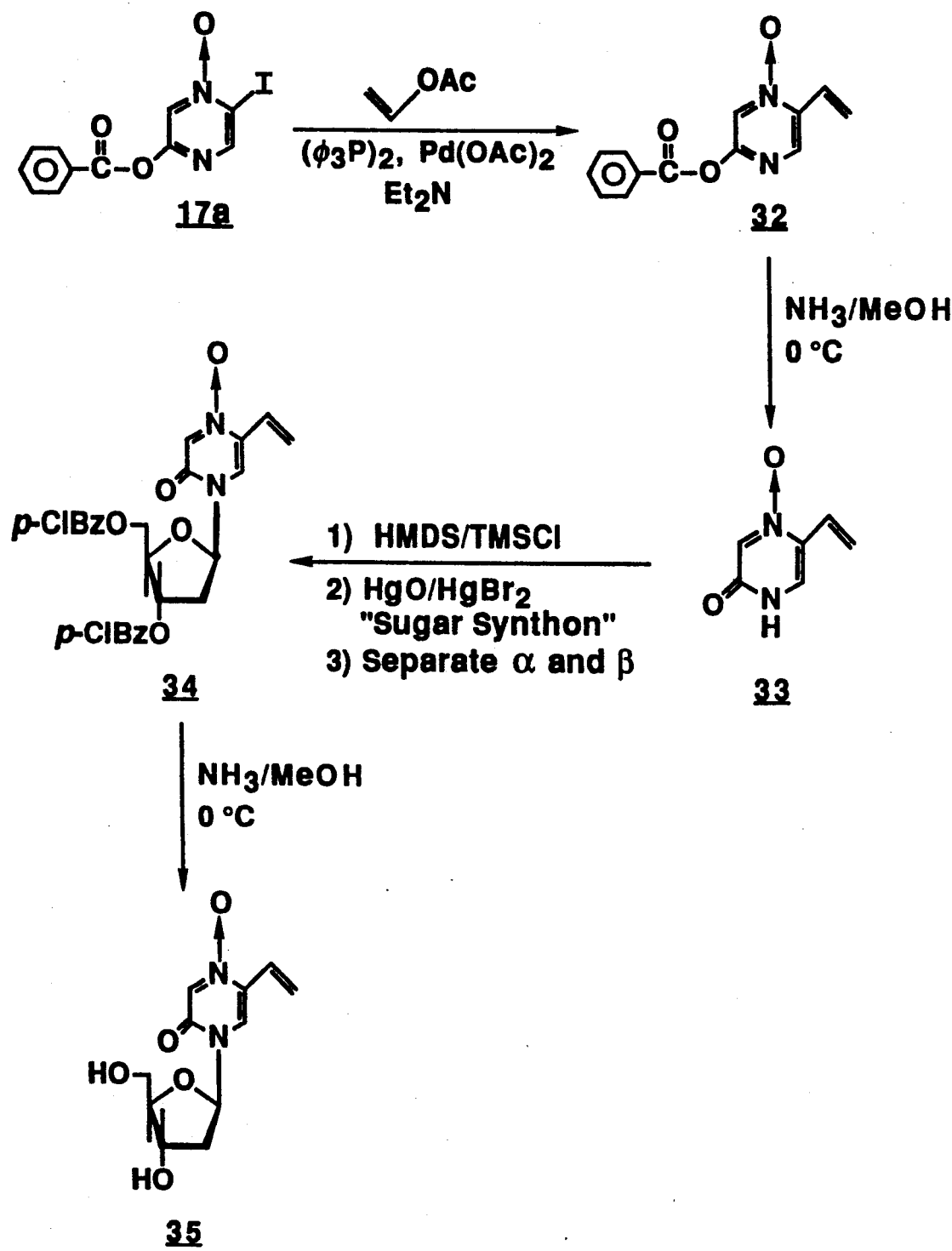

FIGURE 7 - SCHEME VII
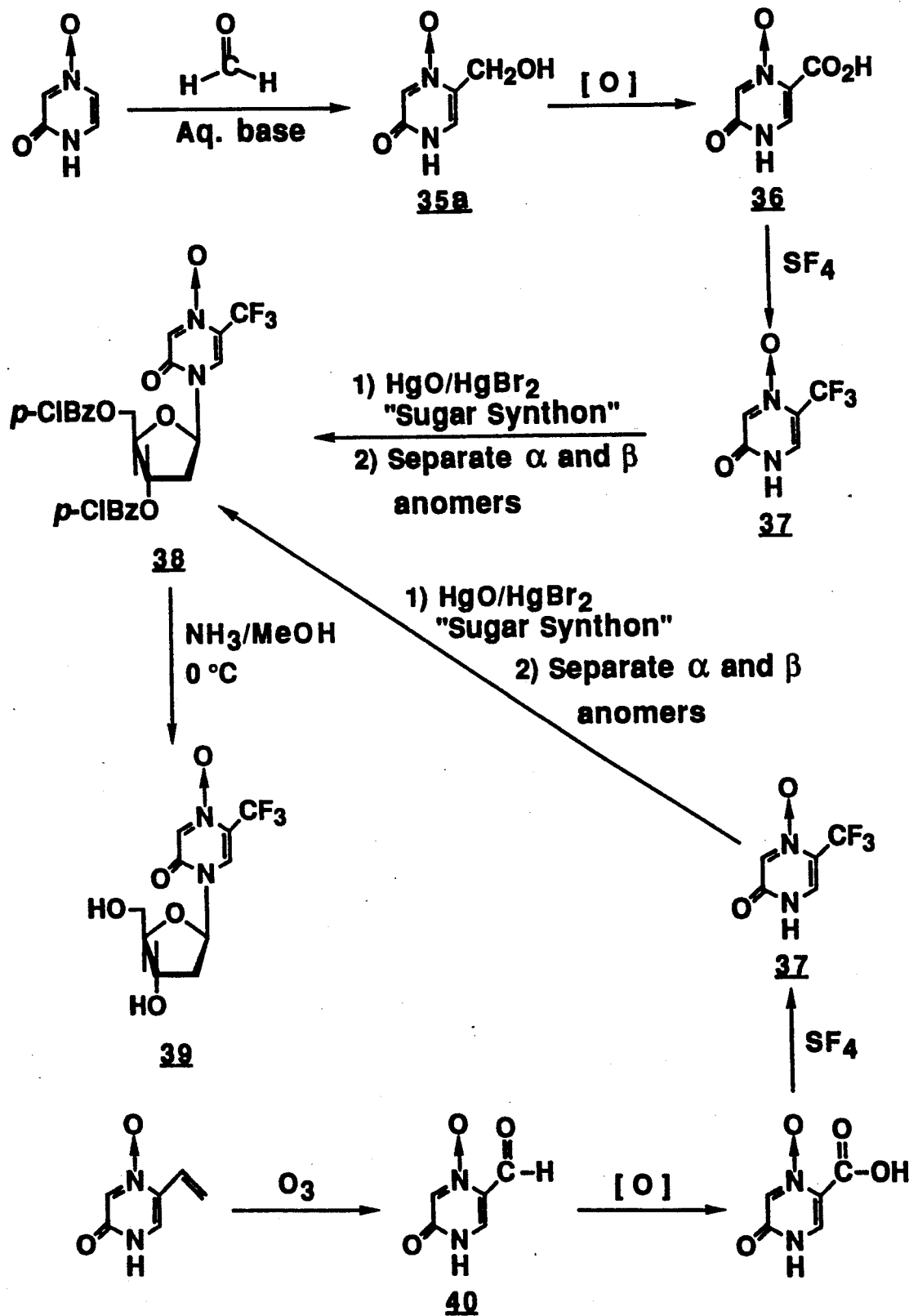

FIGURE 8 - SCHEME VIII
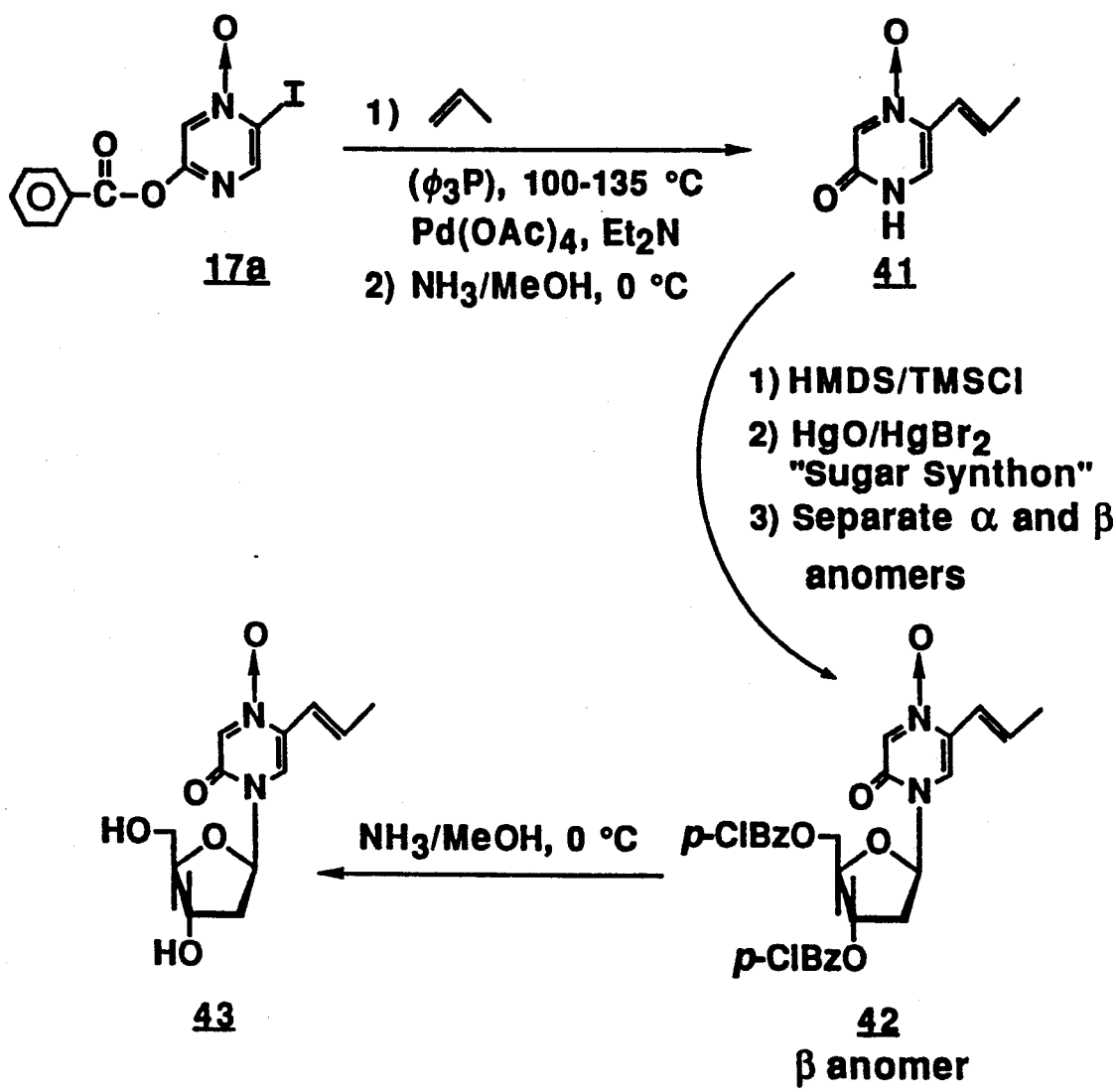

FIGURE 9 - SCHEME IX
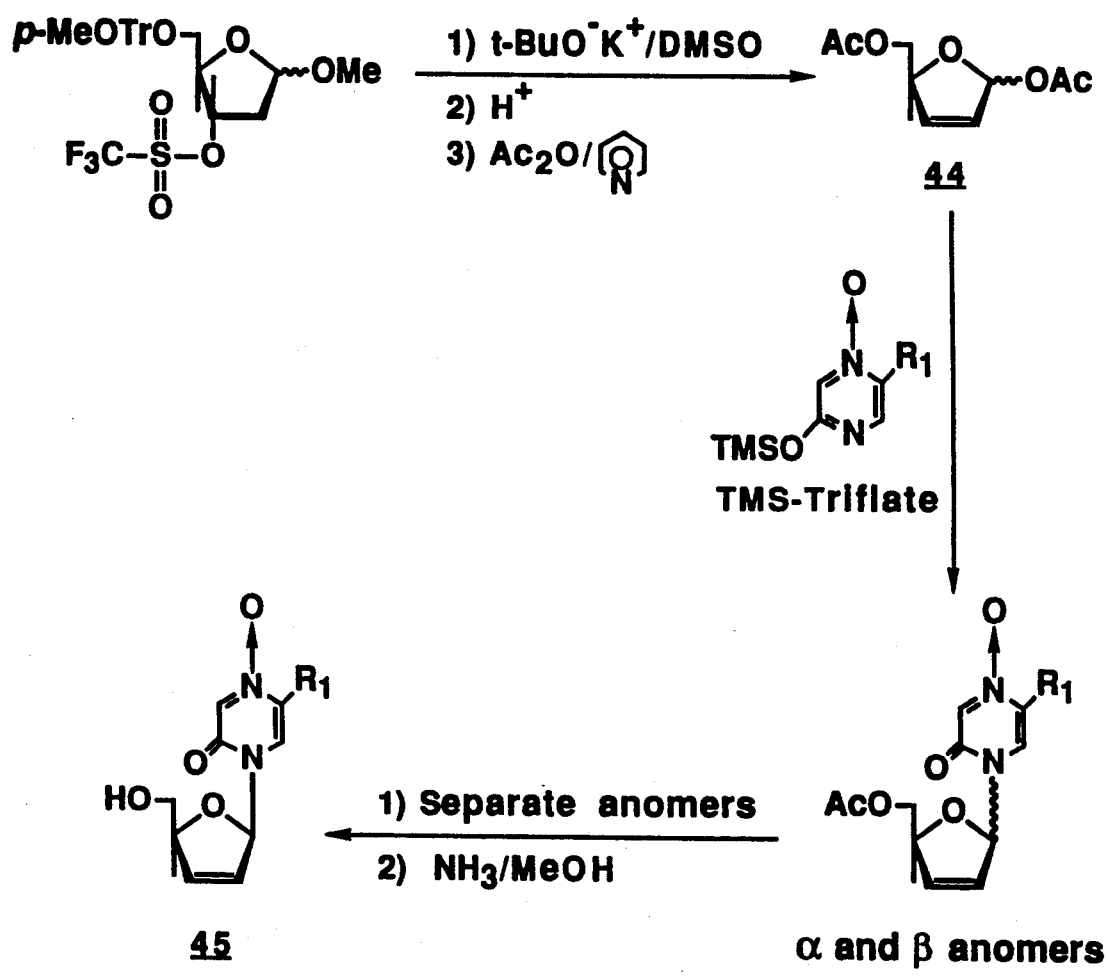

FIGURE 10 - SCHEME X
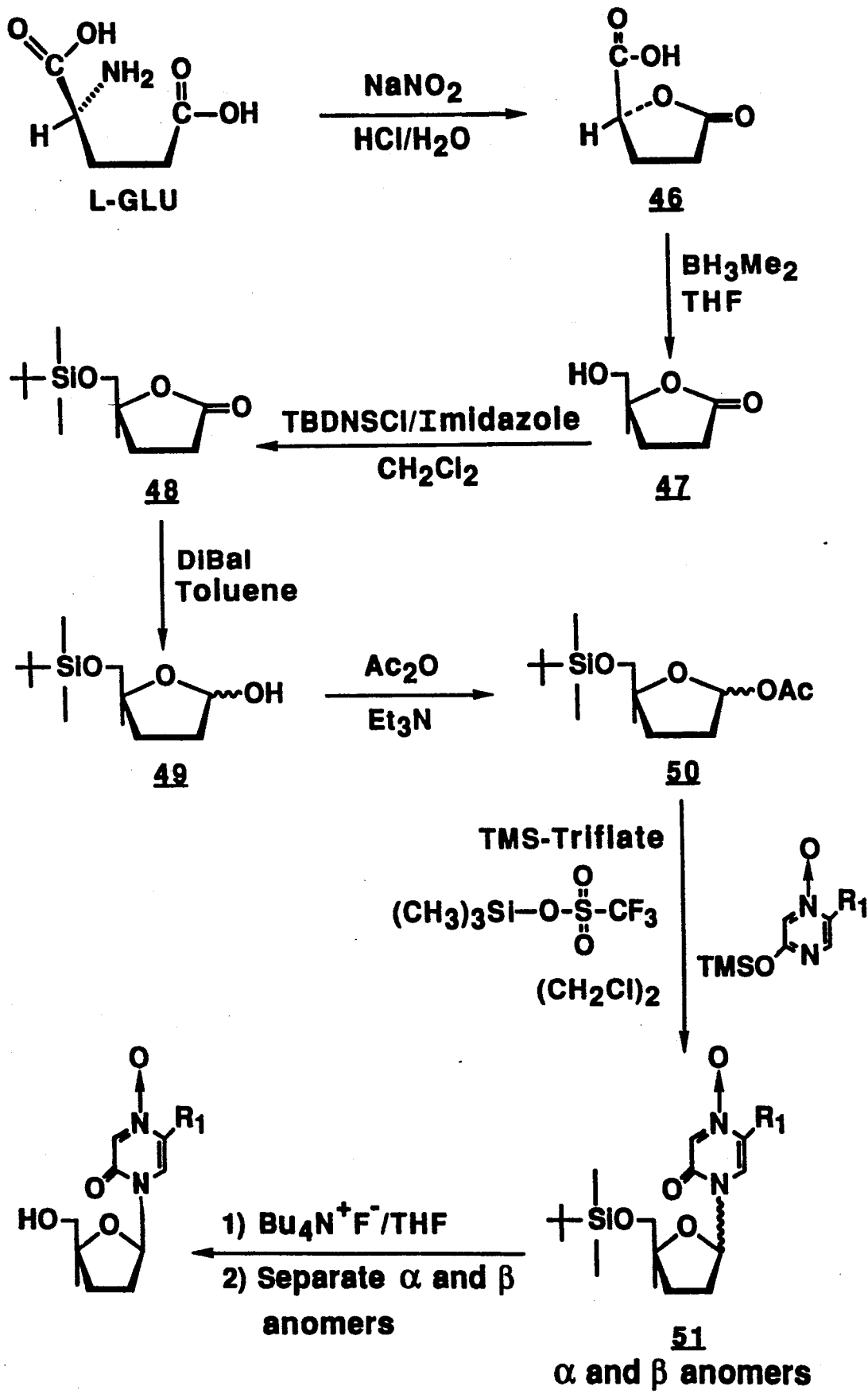

FIGURE 11 - SCHEME XI
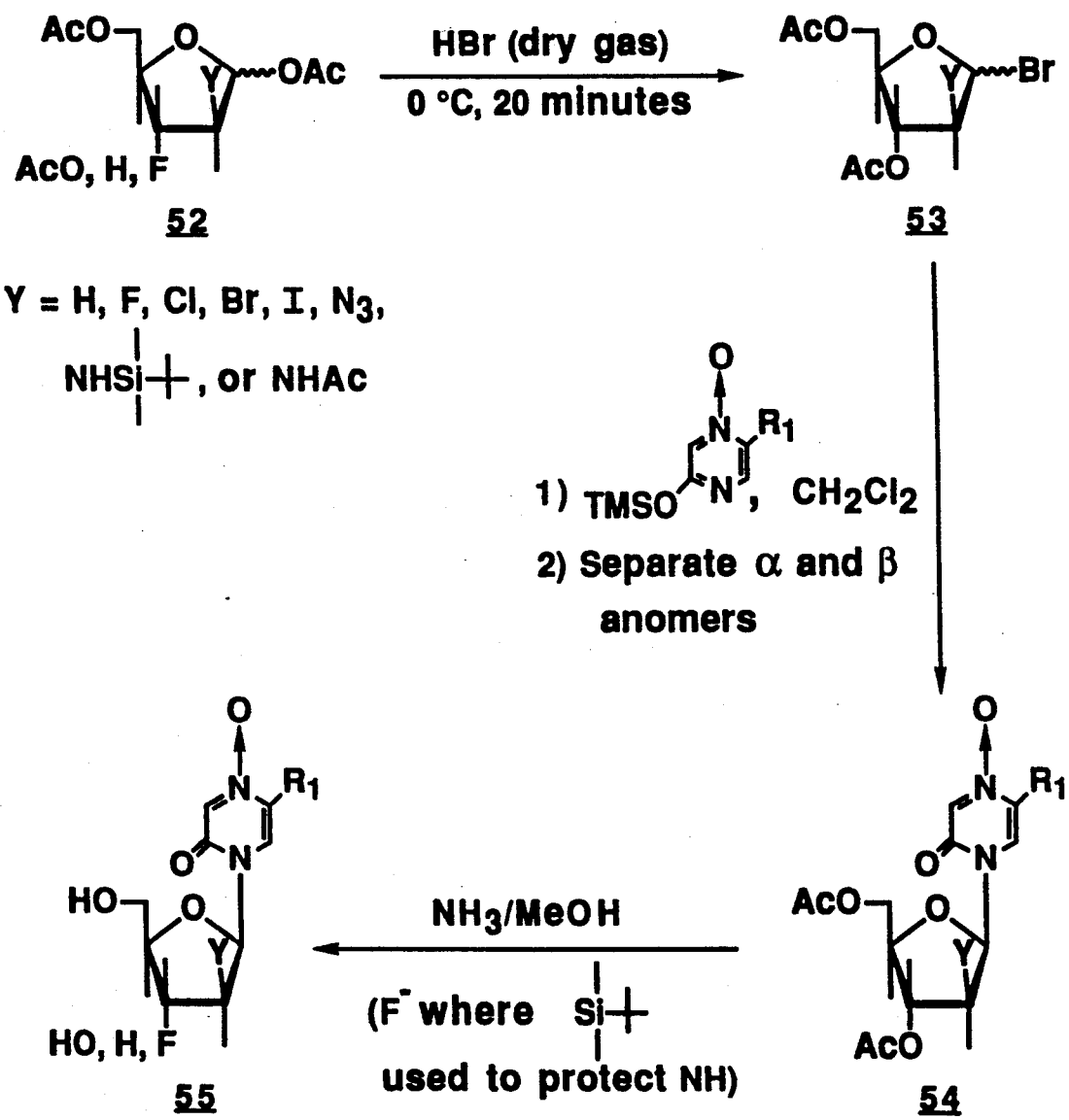

FIGURE 12 - SCHEME XII
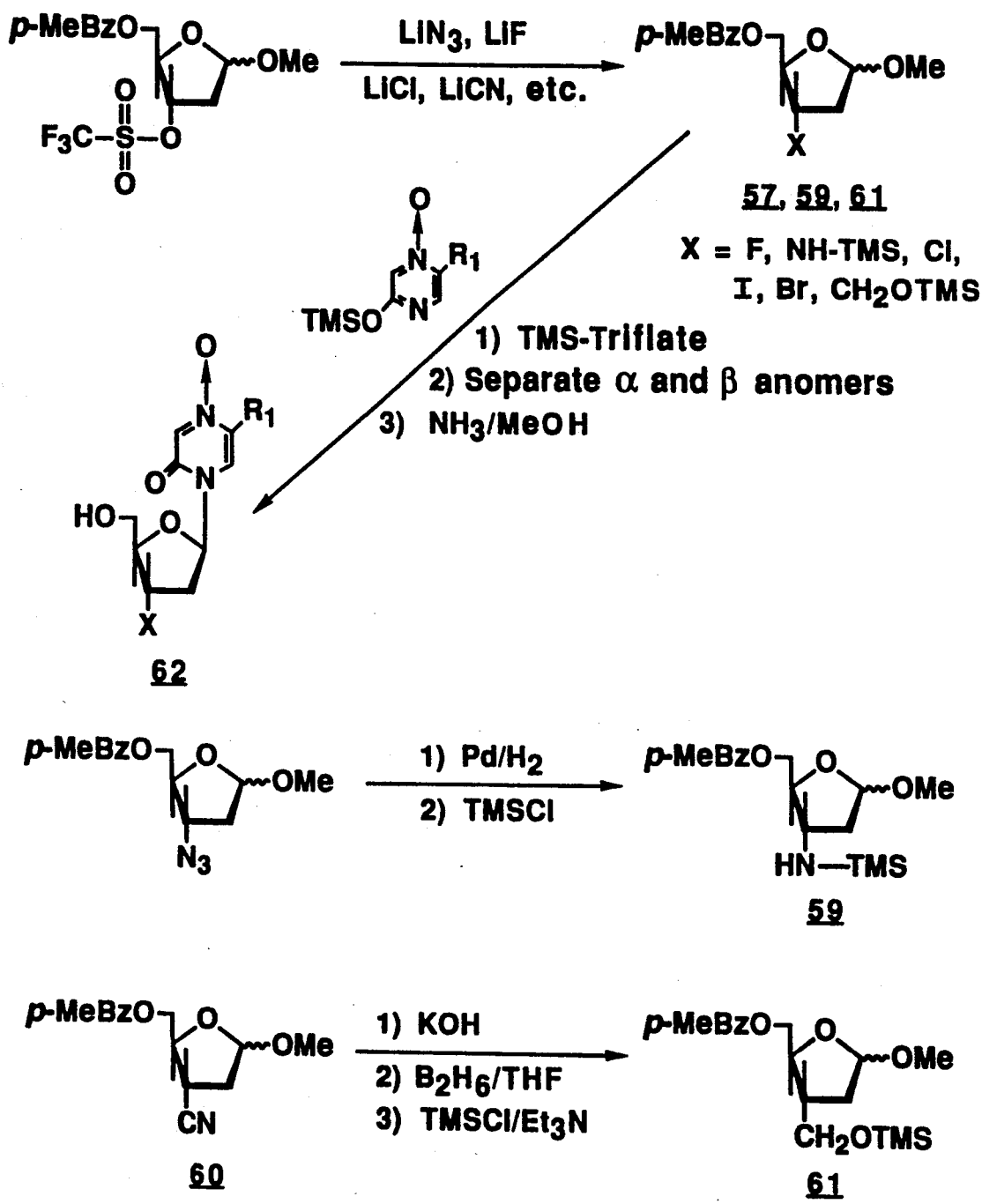

FIGURE 13 - SCHEME XIII
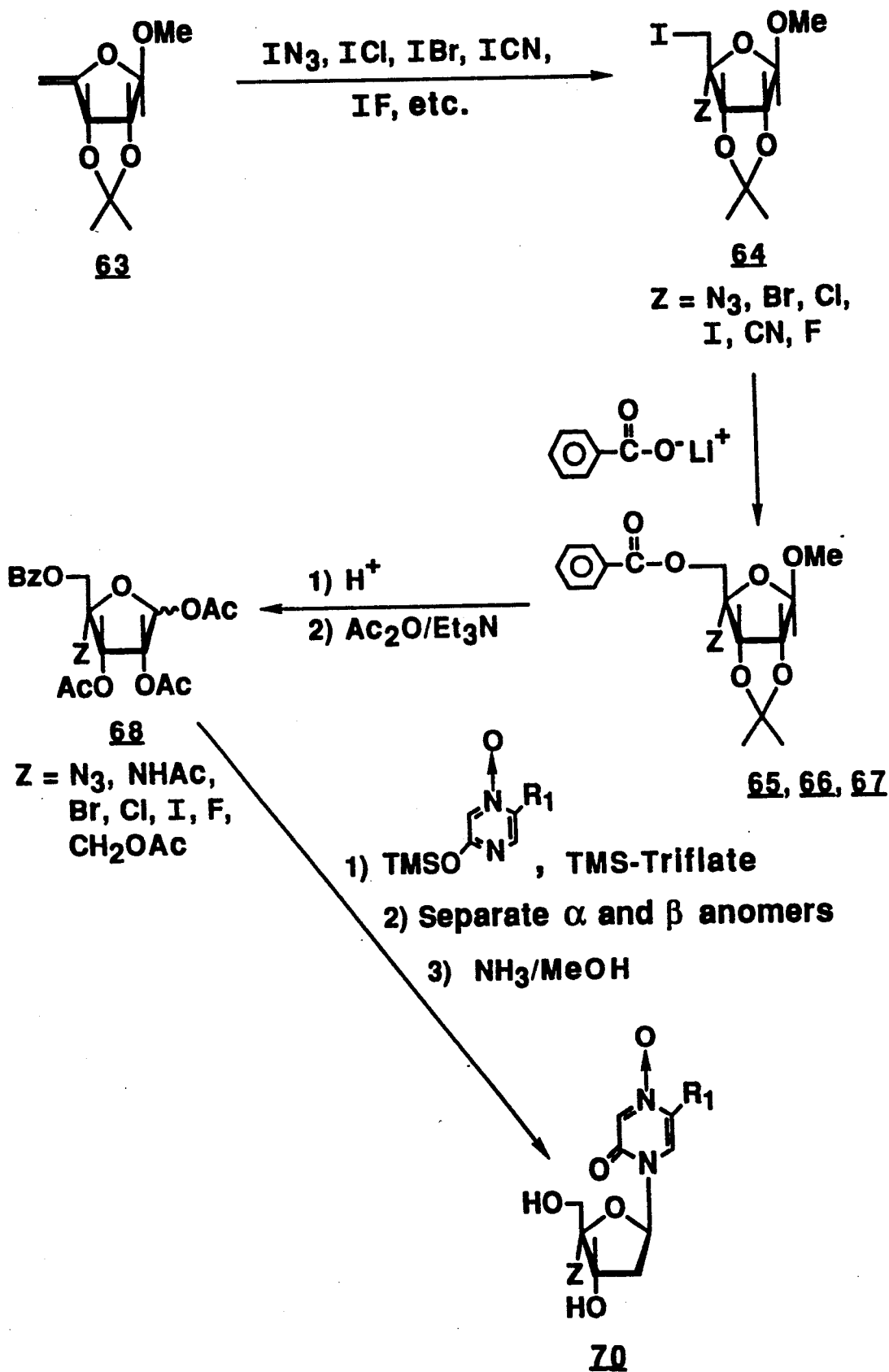

FIGURE 14 - SCHEME XIV
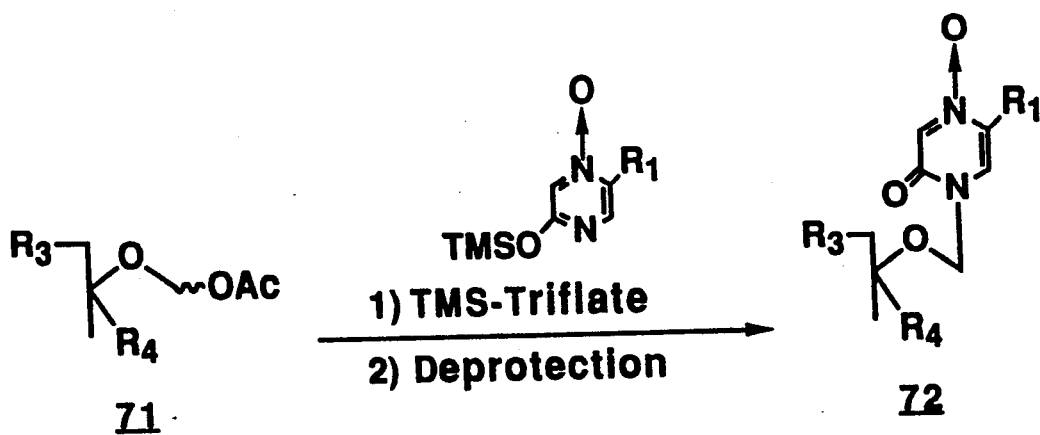
$R_3$ = H, F, Br, Cl, I, OH
$R_4$ = H, $CH_2OH$, $CH_2N_3$, $CH_2NH_2$, OH, F, Br, Cl, I,
OH, $NH_2$, and $CH_2OH$ groups are blocked with TMS groups.

FIGURE 15 - SCHEME XV
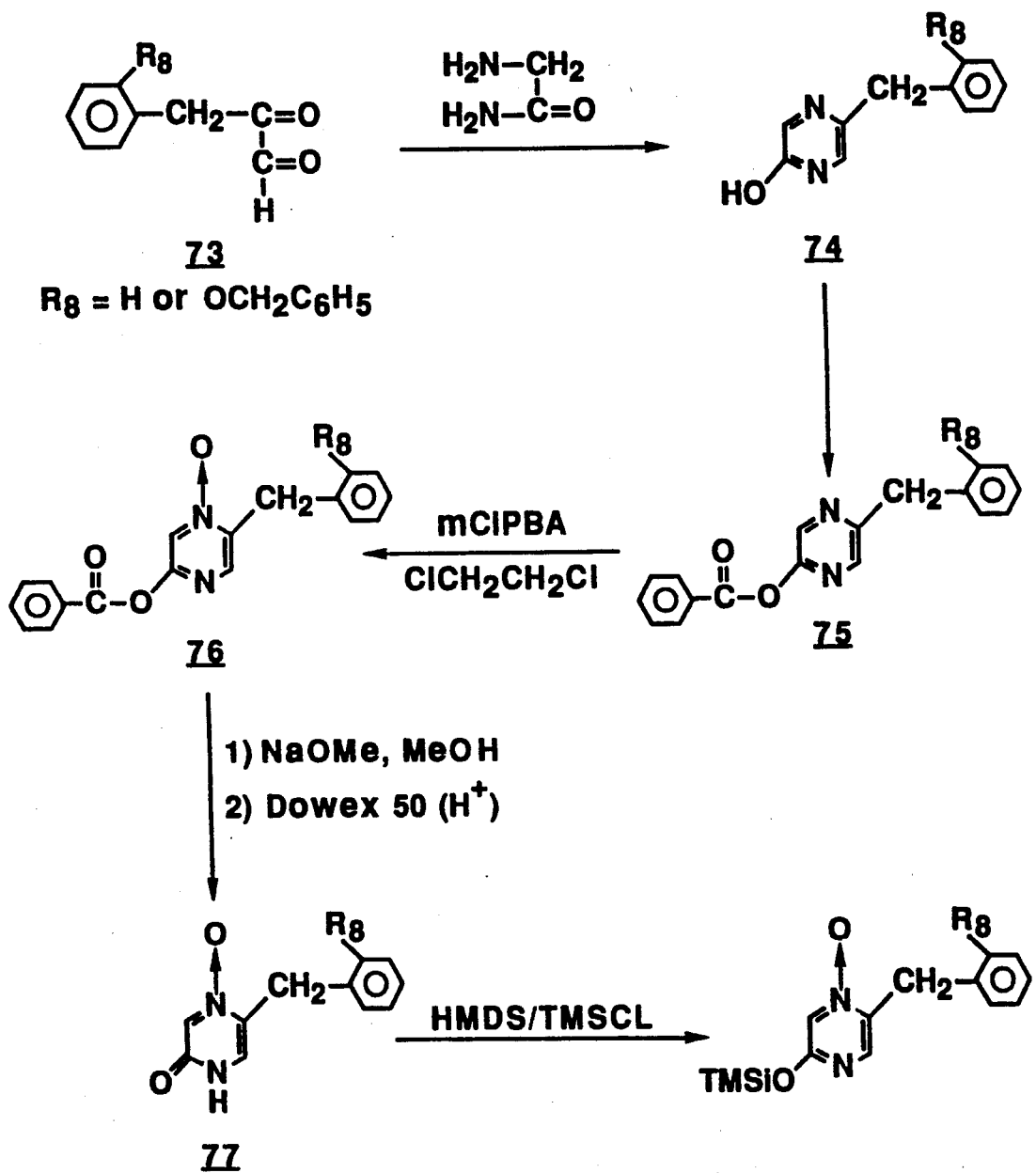

FIGURE 16 - SCHEME XVI
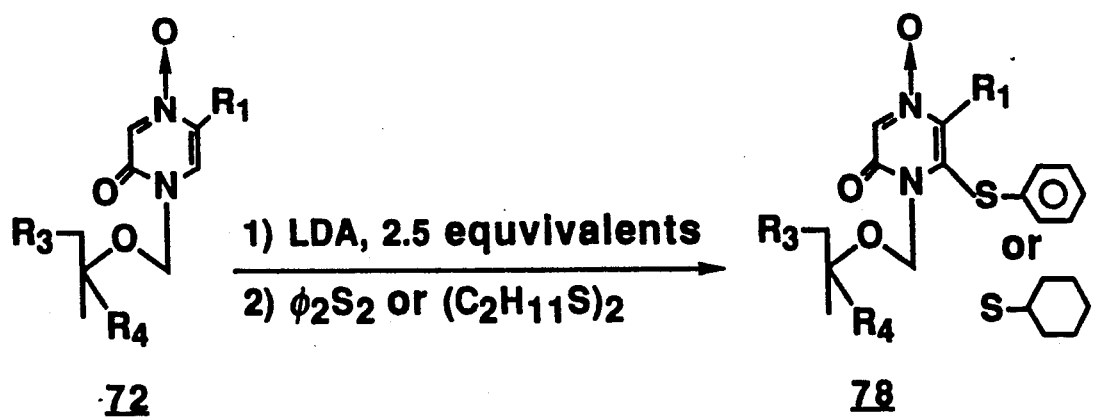
R$_3$ and R$_4$ are protected where required.

FIGURE 17 - SCHEME XVII
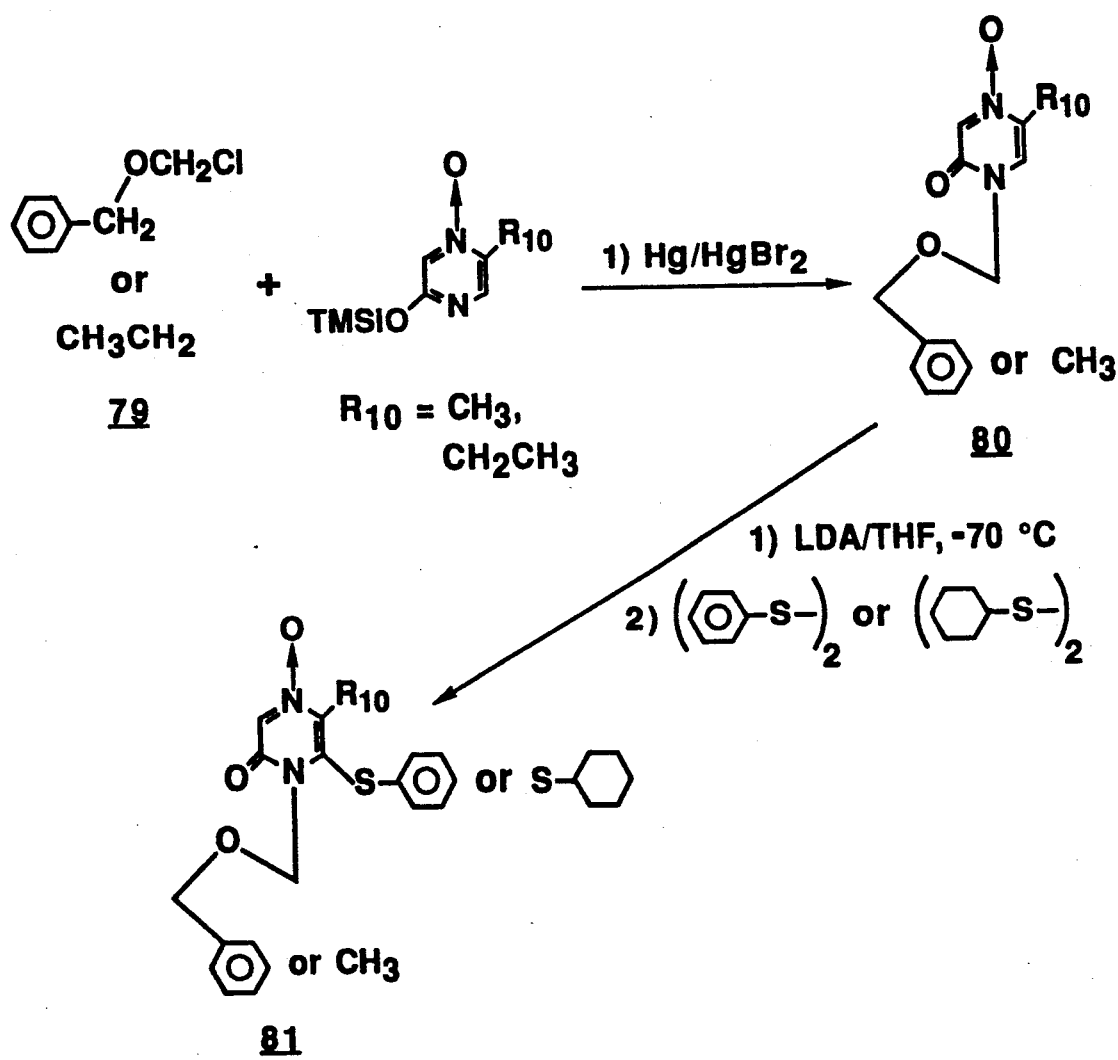

PYRAZINONE N-OXIDE NUCLEOSIDES AND ANALOGS THEREOF

This work is supported by the National Cancer Institute, National Institutes of Health, grant numbers CA-44358 and CA-06695 and National Institute of Arthritis and Infectious Diseases, National Institutes of Health, grant number AI-29430. The government retains certain rights in the invention.

FIELD OF THE INVENTION

This invention relates to nucleoside and acyclo analogs containing 5- and 6- substituted 2-pyrazinone-4-N-oxide These compounds are useful for treating various conditions including viral infections, cancer, fungal infections, bacterial infections, microbial infections and related disease states. This invention also relates to pharmaceutical formulations containing these compounds In addition, this invention relates to methods of treating the above-described conditions in animals and in particular, humans.

BACKGROUND OF THE INVENTION

Viral infections in mammals, and especially in humans, are very widespread and in spite of the considerable progress made in general chemotherapy, little progress has been made in creating specific drugs which either cure viral diseases or alleviate symptoms of patients afflicted with these diseases.

The use of various nucleoside analogs as agents for the treatment of cancer, fungal infections, bacterial infections and viral infections is not new. In the treatment of viral infections, the treatment of Herpes Simplex Virus (HSV), related Herpes infections and Human Immunodeficiency Virus (HIV) with nucleoside analogs is now part of the armamentarium of the medical practitioner.

Unlike the design of anti-cancer or anti-bacterial agents, the design of antiviral agents is generally more difficult. This difficulty is due to the absence of clearcut qualitative differences in the biochemistry of infected and host cells. Because viral infection results in the takeover of the replicative mechanism of infected host cells, the targeting of DNA and its constituent bases as a means of antiviral agent design has been pursued with some success. Various purine and pyrimidine analogs have been synthesized in pursuit of more effective chemotherapeutic agents. In particular, thymidine, a base exclusive to DNA, has become a primary target for structural modification to obtain selective antiviral agents.

A number of pyrimidine nucleoside analogs have shown significant activity as antiviral agents, particularly against the herpes group of viruses. The herpes viruses that infect humans comprise 5 different groups and include Herpes Simplex Virus Types I and II (HSV I and II), which are responsible for herpes labialis, herpes keratitis, herpes encephalitis and herpes genitalis, Varicella Zoster (VZV), which is responsible for chicken pox and shingles, Cytomegalovirus (CMV), which is responsible for neonatal disease and Epstein-Barr Virus (EBV), which is responsible for infectious mononucleosis and Burkitt's lymphoma.

Herpes viruses have been known to cause cancer in animals and there is sufficient evidence suggesting a close relationship between these viral infections and human malignancies (See, for example, Shugar, *FEBS Lett.*, 40, S48, 1974; *Cancer Research*, 34, 1083, 1974; and *Federation Proc.*, Part I, 31, 1625, 1974). Consequently, certain antiviral agents have direct usefulness in antitumor chemotherapy.

Viral infection manifests itself by overtaking the host cell's replication mechanism. Consequently, there exist certain enzymes which are necessary for elaborating the virus via this mechanism. Selective antiviral agents may be designed to target a unique property of the virus-induced enzyme which is not shared by the corresponding host enzyme. Two of these target enzymes in the herpes group of viruses include virus encoded thymidine kinase and DNA-polymerase (Davis, et al., *J. Virol.*, 13, 140, 1974). In those viruses which produce Acquired Immunodeficiency Syndrome (AIDS), the viral replication mechanism often proceeds through an RNA dependent DNA polymerase or Reverse Transcriptase, which may serve as a potential target for anti-AIDS compounds.

The first of the above-mentioned enzymatic targets, viral-induced thymidine kinase, is responsible for the phosphorylation of deoxythymidine to deoxythymidine monophosphate (dTMP). This virus-induced enzyme is synthesized in the infected cell, upon infection with a virus. However, the host cell generally also contains its own thymidine kinase, usually of two major types; cytoplasmic and mitochondrial.

The second potential enzyme target includes the Viral-induced DNA polymerase(s), which are responsible for the biosynthesis of viral DNA. This enzyme(s) functions to replicate the virus and induce the various enzymes that are responsible for viral function.

These two viral enzymes are useful targets for antiviral agents. An agent that could target the viral-induced thymidine kinase or DNA polymerase(s) without interfering with the human thymidine kinase would be a potential therapeutic agent for viral infections.

Certain nucleoside analogs have been shown to be useful as antiviral agents, but also have evidenced certain limitations. For example, 5-substituted deoxyuridine analogs, such as 5-ethyl, 5-propyl and 5-allyl deoxyuridine derivatives have been shown to be alternate substrates for thymidine kinase and have shown selected affinity for the viral-induced thymidine kinase (Cheng, et al., *Antimicrob. Agents and Chemotherapy*, 10, 119, 1976). However, these nucleoside derivatives were found to be substrates for the host enzyme, human thymidine phosphorylase, one of the enzymes which is responsible for thymidine degradation.

Other nucleoside analogs that have shown to be effective antiviral agents against HSV and VZV include acyclovir (ACV), bromovinyl deoxyuridine (BVDU) and 2,-fluoro-5-iodo-arabinosylcytosine (FIAC) (Schaeffer, et al., *Nature*, 272, 583 1978; Elion, et al., *Proc. Nat. Acad. Sci. USA*. 74, 5716, 1977; De Clercq, et al., *Proc. Nat. Acad. Sci. USA,*, 76, 2947, 1979; Watanabe, et al., *J. Med. Chem.*, 22, 21, 1979; Fox, et al., *Antiviral Chemo.*. 219, 1981; Davis, et al., *J. Virol.*, 26, 603, 1978; Allaudeen, et al., *Proc. Nat. Acad. Sci. USA*, 78, 2698, 1981; and De Clerq, E., *Pure and Appl. Chem.*, 55, 623 1983). These compounds are selectively phosphorylated by viral thymidine kinase and their phosphorylated forms inhibit the viral DNA polymerase.

Another viral disease which recently has been studied greatly and treated with only limited success is AIDS. AIDS is a generally fatal disease caused by a human pathogenic retrovirus known as human T-lymphotropic virus type III (HTLV III), lymphadenopathy-associated virus (LAV) or human immunodeficiency virus (HIV). (Barre-Sinoussi, et al., *Science*, 220, 868, 1983 and Mitsuya, et al., *Proc. Nat. Acad. Sci. USA*, 82, 7096, 1985).

In comparison with the other T-lymphotropic retroviruses HTLV I and II, HTLV III (HIV) and lymphoadenopathy viruses are nontransforming cytopathic viruses without immortalizing activity. The viral replication process is believed to be an important event in the progress of AIDS. It is further believed that the enzyme Reverse Transcriptase plays an essential role in the elaboration and life cycle of HIV and consequently, the progress of the disease. It is therefore believed that this enzyme may be a particularly appropriate target for the development of potential drugs against AIDs because of the absence of such an enzyme in the uninfected host cell.

Recently, investigators have studied a number of antiviral agents as potential anti-AIDS agents, e.g., ribavirin (See, for example, McCormick, et al., *Lancet.* ii. 1367, 1984; Gilbert and Knight, *Antimicrobial Agents and Chemotherapy*, 30, 201, 1986; and Robins, et al., *Adv. Enzyme Regul.*, 24, 29, 1986) and Suramin (Mitsuya, at al., *Science.* 226, 172, 1984), among others. A number of nucleosides have played important roles in the treatment of RNA and DNA viral diseases. 3'-azido-3'deoxythymidine (AZT) and 2',3'-Dideoxynucleosides, for example, 2',3'-dideoxycytidine (DDC) and 2',3'-dideoxyadenosine and 2',3'-dideoxyinosine, among other nucleosides, have shown promise as potential anti-AIDS agents (Richman, et al., *N. Engl. J. Med.*, 317, 192 1987; and Mitsuya, *Proc. Nat. Acad. Sci. USA.* 83, 1911, 1986). Certain of these 2',3'-dideoxynucleosides of cytidine and adenosine in the form of their respective 5'-triphosphate derivatives can act as chain terminators because of their lack of a 3'-hydroxyl group for forming a phosphotriester linkage. Other thymidine and cytidine derivatives such as 3'-amino, 3'-azido and 2',3'L- dideoxy-2',3'-didehydro analogues have also exhibited anti-HIV activity (Lin and Prusoff, *J. Med. Chem..* 21, 109, 1978; Balzarini, et al., *Mol. Pharmacol.*, 32, 162, 1987; Kim, et al., *J. Med. Chem.*, 30, 862, 1987; Baba, et al., Biochem. Biophys. Res. Comm., 142, 128, 1987; Lin, et al., *J. Med. Chem.*, 30, 440, 1987; and Lin, et al., *Biochem. pharmacol.*, 36, 311, 1987).

Certain biological characteristics of nucleoside analogs in general may limit their use as anti-viral agents. These characteristics include their toxicity, metabolic inactivation (by for example, cytidine deamination and thymidine and uridine phosphorylation) and lack of selectivity (Holy, *Nucleosides and Nucleotides*, 81, 147, 1978). In certain cases, these agents may be incorporated into DNA, resulting in teratogenicity and mutagenicity (Renis, *Antiobiotics Chemother.*, 27, 164, 1980).

Metabolic inactivation is a common mechanism by which certain nucleosides are limited in therapeutic value. For example, although anti-viral activity has been demonstrated by a number of 2'-deoxyuridine derivatives containing 5-substituents such as 5-iodo, bromo, ethynyl, propyl, trifluoromethyl, ethyl, S-methyl, nitro, cyanato, iodovinyl, and bromovinyl, among others. (See, for example, Rapp and Vanderslice, *Virology*, 22, 321, 1964; Rawls, et al., *Proc. Soc. Exp. Biol. Med.*, 115, 123, 1964; Prusoff and Ward, *Biochem. Pharmacol.*, 25, 1233, 1976; Salzman, *Virology*, 10, 150, 1960; Kaufman and Heidelberger, *Science*, 145, 585, 1964; Heidelberger and Boohar, Biochem. Biophys. Acta, 91, 639, 1964; De Clercq, et al., *Molec. Phar-* *macol.*, 14, 422, 1978; Nemes and Hilleman, *Proc. Soc. Exp. Biol. Med.*, 119, 515, 1965; De Clercq and Shugar, *Biochem. Pharmacol.*, 24, 1073, 1975; Gupta, et al., *J. Med. Chem.*, 18, 973, 1975; De Clercq, et al., *Antimicrob. Agents Chemother.*, 13, 545, 1978; Cheng, *Biochim. Biophys. Acta,* 452, 370, 1976; Hardi, et al., *Antimicro. Agents Chemother.*, 10, 682, 1976; Kotick, et al., *J. Org. Chem.*, 34, 3806, 1969; Ryu and Bardos, *J. Heterocyc. Chem..* 16, 1049, 1979; Torrence, et al., *J. Med. Chem.*, 20, 974, 1977; Bardos and Kalman, *J. Pharm. Sci.*, 55, 606, 1966; and De Clercq, et al., *J. Med. Chem.*, 26, 661, 1983), their corresponding cytidine analogs undergo the above-mentioned enzymatic deamination to give compounds with less or no activity, this cripples their biological utility. Those degradation products which are thymidine analogs further limits their utility because they are generally substrates for thymidine phosphorylase (metabolic inactivation) (Schroeder, et al., J. Med. Chem., 24, 109, 1981).

The antiviral activity of certain of these nucleosides is believed to be due, at least in part, to their conversion into triphosphates followed by their incorporation into DNA (See, Stellwagen and Tompkins, *Proc. Natl. Acad. Sci. USA,* 68, 1147, 1971; Stellwagen and Tompkins, *J. Mol. Biol.*, 56, 167, 1971; Graham and Whitmore, *Cancer Res.*, 30, 2636, 1970; and Dannenberg and Heidelberger, *J. Med. Chem.*, 16, 712, 1973). This, unfortunately often produces mutagenic effects in the host organism, especially for such analogues as 5-iodo-2'-deoxyuridine. However, such mutagenic effects are minimal for certain analogues which exhibit base-pairing properties in DNA which are similar for those of the parent base. This is true for 5-ethyl, propyl and $SCH_3$ derivatives of 2'-deoxyuridine. In particular, 5-ethyl-2'-deoxyuridine has been found to have significant activity against herpes simplex and vaccinia viruses, comparable to that of 5-iodo-2'-deoxyuridine, but without the concomitant mutagenicity (Bernaerts and De Clercq, *Nucleosides and Nucleotides,* 6, 421, 1987; Kulikowski, and Shugar, *J. Med. Chem.*, 17, 269, 1974; and Swierkowski and Shugar, *J. Med. Chem.*, 12, 533, 1969).

A number of 5-substituted 2-pyrimidinone-2'-deoxynucleoside analogs, including methyl-, fluoro-, iodo-, bromo-, ethynyl and propynyl- have also been shown to exhibit antiviral activity, apparently by inhibiting virus specific thymidine kinase (Efange, et al., *J. Med. Chem.*, 28, 904, 1985 and Lewandowski, et al., *Antimicrob. Agents and Chemother.*, 33, 340, 1989).

Several modifications on the sugars of nucleosides have produced agents having good antiviral activity. Several arabinosides, including ara-C and Ara-T have shown good antiviral activity (Chen, et al., *J. Biol. Chem.*, 251, 4833, 1976; Neenan and Rohde, *J. Med. Chem.*, 16, 580, 1973; and Cheng, et al., *Ann. N.Y. Acad. Sci.,* 255, 332, 1975). Substitutions at the 5'- position with amino, azido groups have rendered highly selective antiherpes agents, whereas substitution at the 3'-position with an azido group has provided potent anti-HIV activity. Several 2',3'-modified nucleosides have been studied for antiherpes activity and several 2',3'-dideoxy-2',3'-didehydro and dideoxy compounds have shown activity against a variety of viruses, particularly HIV.

Very little work has been done on 5-substituted 2-pyrazinone N-oxide nucleoside analogs, which is the subject of the present application. The riboside of 2-pyrazinone-4-N-oxide has been found to have antibacterial activity (Bobek and Bloch, *J. Med. Chem.*, 15, 164, 1972). Its 2'-deoxyribonucleoside proved to be significantly more effective as an antimicrobial agent than the riboside, but was essentially inactive against leukemic L1210 cells (Berkowitz, et al., *J. Med. Chem.*, 16, 183, 1973). In contrast, the 2'-deoxyribonucleoside of 5-methyl-2-pyrazinone-4-N-oxide was found to be significantly more active against leukemic L1210 cells and only marginally active against the bacterial cells (Bobek and Bloch, *J. Med. Chem.*, 20, 458, 1977). None of these agents have been shown to be effective as antiviral agents.

BRIEF DESCRIPTION OF THE INVENTION

The compounds of the present invention are nucleosides and related analogs containing 5- (and in certain cases 6-) substituted 2-pyrazinone-4-N-oxide. These agents are useful for treating one or more of various conditions including viral infections, cancer, fungal infections, microbial infections and related disease states. In addition, certain of these agents are useful as biological modifiers or as intermediates for producing related chemical species. Compounds of the present invention find particular use in combating viral infections which afflict animals, in particular, humans and offer great potential as alternatives for or in combination with agents which are presently available. The compounds of the present invention are based upon the substitution of the 5-or 6-position of 2-pyrazinone-4-N-oxide with a variety of moities to produce 2'-deoxynucleosides and related analogs including acyclo analogs having the above-mentioned utility. The compounds of the present invention are also based on a number of modifications of the sugar moiety or a related moiety.

The present invention also relates to therapeutic methods for treating viral infections comprising administering anti-viral effective amounts of the therapeutic compositions to treat viral infections including HSV (I and II), VSV, EBV, CMV and HIV infections.

Pharmaceutical compositions based upon these novel chemical compounds comprise the above-described compositions in a therapeutically effective amount, optionally in combination with a pharmaceutically acceptable additive, carrier or excipient.

While not being limited by way of theory, it is believed that the compositions according to the present invention act as antiviral, antibacterial, antifungal and anticancer agents by functioning as anti-metabolites for enzymes and enzyme systems that are necessary for the function or advancement of the disease state or condition treated. It is also possible that certain of these compositions may also function by incorporating into the DNA of the disease organism or cell. In addition, the compositions according to the present invention are useful as biological modifiers and as chemical intermediates in the synthesis of biologically active compositions.

BRIEF DESCRIPTION OF THE FIGURES

FIGS. 1-17 (Schemes I-XVII) depict the synthetic chemical steps which are used to synthesize the compositions according to the present invention. Schemes pertaining to the synthesis of a particular composition are referenced in the examples set forth herein.

DETAILED DESCRIPTION OF THE PRESENT INVENTION

The following definitions will be used to describe the present invention.

The term "biological modifier" will be used throughout the specification to describe a composition according to the present invention which can be used in combination with an additional biologically active composition to modify or enhance the biological activity of that additional biologically active composition. While not being limited by way of theory, it is believed that certain of the compositions according to the present invention may inhibit certain of the degradative or metabolic enzymes which metabolize biologically active compositions to inactive compositions. In this way, the biological modifiers of the present invention may impact the biological activity of biologically active compositions which are co-administered with these biological modifiers.

The term "microbial" is used throughout the specification to describe infections which are caused by microorganisms including bacterial infections, infections by parasites, mycoplasma, spirochetes, rickettsiae and microscopic and ultramicroscopic organisms.

The term "sugar" is used throughout the specification to describe those carbohydrate moieties generally containing five carbons, such as ribofuranose, arabinofuranose and related substituted and protected carbohydrate moieties which are condensed onto the N-1 position of the 5-substituted-2-pyrazinone-4-N-oxide derivatives of the present invention.

The term "sugar synthon" is used throughout the specification including the chemical synthetic schemes to describe a blocked and/or substituted sugar which is condensed onto the N-1 position of the 5-substituted 2-pyrazinone-4-N-oxide derivatives of the present invention.

The term "protect" or "block" is used throughout the specification to describe a well-known chemical moiety which is temporarily bonded to a hydroxyl, amine, keto or related active group which, without the protecting group, would participate in a reaction in an undesireable manner. After a particular reaction has been completed, protecting or blocking groups are easily removed using standard techniques available in the art.

The term "acyclo" is used throughout the specification to describe any non-cyclic moiety which is condensed onto the N-1 position of the 5-substituted-2-pyrazinone-4-N-oxide derivatives of the present invention.

The term "mole percent" or "mole %" is used throughout the specification to describe the percent in moles of a particular reagent utilized in a synthetic pathway with reference to a first reagent. For example, if a reaction describes the use of a first reagent and "100 mole percent of a second reagent", the amount of the second reagent utilized is equal to the identical amount of the first reagent in moles. 1.5 mole percent of a second reagent is equal to 1.5% of the number of moles of the first reagent. 100 mole percent is synonymous with "1 equivalent."

The term "didehydro" is used throughout the specification to describe sugar moieties which contain a double bond. For example, 2',3'-didehydro refers to a sugar moiety containing a double bond between the 2' and 3' carbons of the sugar.

The term "herpes related disease" is used throughout the specification to describe a disease caused by any one or more of the following viruses: HSV I, HSV II, Varicella Zozter (VZV), Cytomegalovirus (CMV) and Epstein-Barr Virus (EBV) which produce the following conditions: herpes labialis, herpes keratitits, herpes encephalitis, herpes genitalis, chicken pox, shingles, certain neonetal disease, infectious mononucleosis and Burkitt's lymphoma.

The present invention relates to a first group of compositions (Group I) of the general structure:

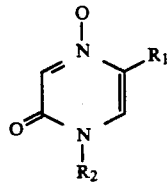

where
$R_1$ is H, $CH_3$, $C_2H_5$, $C_3H_7$, i—$C_3H_7$, —$CH_2$—$C_6H_5$, —CH=$CH_2$, —CH=CH—$CH_3$,

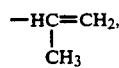

—C≡CH, —C≡C—$CH_3$, —C≡C—$C_6N_5$, I, Br, $CF_3$, —CH=CHBr, or —CH=CC$_6$H$_5$;
$R_2$ is

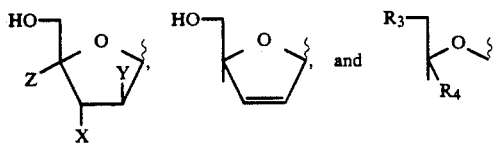

such that
X is H, OH, $CH_2OH$, $N_3$, $NH_2$, F, Cl or I, when Y is H, F or OH and Z is H or F;
Y is H, OH, $N_3$, $NH_2$, F, Br, Cl or I, when X is H, F or OH and Z is H or F;
Z is H, $CH_2OH$, F, Cl, I, $N_3$ or $NH_2$, when X and Y are H, F or OH,
provided that $R_1$ is not H or $CH_3$ when Y=Z=H and X=OH;
$R_3$ is H, F, Br, Cl, I or OH; and
$R_4$ is H, $CH_2OH$, $CH_2N_3$, $CH_2NH_2$, OH, F, Br, Cl or I.

Preferred compositions according to the present invention include those compositions where $R_2$ is

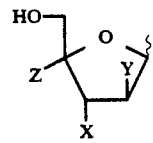

such that X is H, OH, $N_3$ or F and Y is OH or H and Z is H. Additional preferred compositions include those where $R_1$ is $CH_3$, $C_2H_5$, H, CH=$CH_2$ or CH=CHBr. Most preferably $R_1$ is $CH_2CH_3$, X is OH and Y and Z are H.

Other preferred compositions include those where $R_2$ is

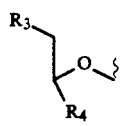

where $R_3$ is OH, $R_4$ is H and $R_1$ is H, $CH_3$, $C_2H_5$ or I.

The present invention also relates to a third group of compositions (Group III) of the general structure:

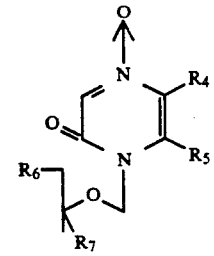

where
$R_4$ is H, $CH_3$, $C_2H_5$, $C_3H_7$, i-$C_3H_7$, —$CH_2$—$C_6H_5$, —CH=$CH_2$, —CH=CH—$CH_3$,

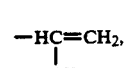

—C≡$CH_2$, —C≡C—$CH_3$, —C≡C—$C_6H_5$, I, Br, $CF_3$, —CH=CHBr, or —CH=CC$_6$H$_5$;
$R_5$ is S—$C_6H_5$ or —S—$C_6H_{11}$;
$R_6$ is H, OH, F, Br, Cl, I, $N_3$ or $NH_2$; and
$R_7$ is H, OH, $N_3$, $NH_2$, $CH_2OH$, $CH_2N_3$, $CH_2NH_2$, F, Br, Cl or I.

Preferred compositions include those where $R_6$ is OH and $R_7$ is H and other preferred compositions include those where $R_4$ is $CH_3$ or $C_2H_5$. $R_5$ is preferably S-$C_6H_5$.

The present invention also relates to a third group of compositions (Group III) of the general structure:

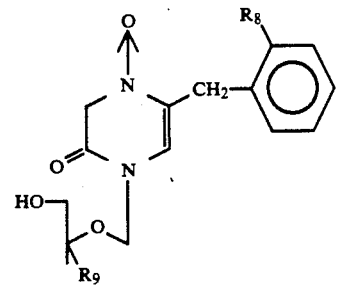

where $R_8$ is H or —$OCH_2C_6H_5$; and where $R_9$ is H, $CH_2OH$, $CH_2N_3$, or $CH_2NH_2$.

Preferably, in this group of compositions, $R_8$ is $OCH_2C_6H_5$ and $R_9$ is H or OH.

The present invention also relates to a fourth group of compositions (Group IV) of the general structure:

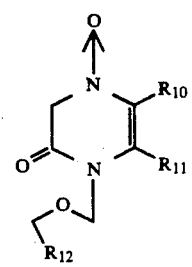

where $R_{10}$ is —$CH_3$ or —$CH_2CH_3$;
$R_{11}$ is S—$C_6H_5$ or S—$C_6H_{11}$; and
$R_{12}$ is —$C_6H_5$ or —$CH_3$.

Preferably, in this group of compositions, $R_{10}$ is $CH_2CH_3$ and $R_{11}$ is $SC_6H_5$.

The compositions of the present invention are useful for their biological activity and in particular, as antiviral, antibacterial, antifungal or anticancer agents. In addition, these compositions may also find use as biological modifiers or as intermediates in the chemical synthesis of other nucleoside or nucleoside analogs which are, in turn, useful as therapeutic agents and other purposes. Preferably, these compositions find use as novel antiviral agents, and in particular as agents to combat herpes related diseases and AIDS.

In general, the most preferred antiviral, antimicrobial and antifungal compounds of the present invention include those which are less cytotoxic and more active. Compositions which find use as anti-cancer agents are generally more cytotoxic than agents which are preferred antiviral, antibacterial or antifungal agents. Compositions according to the present invention which find use as biological modifiers are also less cytotoxic and more active. Certain of the compositions, in pharmaceutical dosage form, may be used as prophylactic agents. These may be particularly appropriate as antiviral agents, and in particular, anti-HSV or anti-HIV agents. In certain pharmaceutical dosage forms, the pro-drug form of the compositions of the present invention are preferred.

The compositions of the present invention are produced by synthetic methods which are readily known to those of ordinary skill in the art and include various chemical synthetic methods as well as enzymatic methods. Two general methods of chemically synthesizing the compositions of the present invention are described. In the first method, the substituents at the 5-position of the 2-pyrazinone-4-N-oxide are first introduced and then the corresponding 5-substituted 2-pyrazinone-4-N-oxide base is subsequently condensed with a sugar or analogous synthon to produce the compositions according to the present invention. Most of the compositions according to the present invention are synthesized in this fashion. In the second method, various substituents, for example, methyl, ethyl, propyl, ethynyl, bromovinyl, bromo, iodo, etc. are introduced at the 5 position of a 2-pyrazinone-4-N-oxide which has been pre-condensed at the N—1 position with a deoxyribosesugar or analogous group by any one of several methods readily available in the art. Often this is a less compatible route because of the difficulty of maintaining the sugar moiety on the base during substitution.

During chemical synthesis of the various compositions according to the present invention, one of ordinary skill in the art will be able to practice the present invention without undue experimentation. In particular, one of ordinary skill in the art will recognize the various steps that should be performed to introduce a particular substituent at the 5 position of the 2-pyrazinone-4-N-oxide base or a substituent at any one or more of the positions on the sugar moiety or analogous moiety. In addition, chemical steps which are taken to "protect" functional groups such as keto, hydroxyl or amino groups, among others, as well as "de-protect" these same functional groups, will be recognized as appropriate within the circumstances of the syntheses.

The compositions according to the present invention exhibit broad biological activity including antiviral, antifungal antibacterial and anticancer activity. Preferably, the agents according to the present invention find utility as antiviral agents, and in particular, as anti-HSV and/or anti-HIV agents. For example, the compositions of Group I, above, especially the 2'-deoxyribonucleosides and the acyclo nucleosides, show activity primarily as anti-HSV agents, but a number of agents within Group I also exhibit cytotoxic activity (anticancer) as well as anti-HIV activity, especially when the 3' is substituted with something other than an OH group, for example, when the compositions are 2'3'-dideoxyribonucleosides. The compositions of Group II, which are substituted at the 5 and 6 position of the 2-pyrazinone-N-oxide base and are acyclo derivatives, exhibit primarily antiviral and in particular, anti-HIV activity. The compositions according to Group III exhibit activity primarily as biological modifiers for enhancing the activity and duration of action of additional agents, but other agents within this Group III also exhibit additional biological, including antiviral activity. The compositions according to Group IV exhibit primarily antiviral, and in particular, Anti-HIV activity. One of ordinary skill in the art will recognize the fact that a particular composition which may appear in a given Group according to the present invention may provide a general understanding as to its biological activity and in certain cases, its mode of action, however, the organization of the presentation of the compositions according to the present invetion should not be taken to limit the biological activity to a particular disease state or condition to be treated.

The present invention also includes pharmaceutical compositions for use in treating patients with various infections and conditions including viral, bacterial, fungal or cancer. In these pharmaceutical compositions an active agent is formulated in a therapeutically effective amount for treating the particular infection or condition. One of ordinary skill in the art will recognize this amount to vary with the infection or condition to be treated, the treatment regimen, the pharmacokinetics of the agent used, as well as the patient (animal or human) treated.

Preferably, the active agent is formulated in admixture with a pharmaceutically acceptable carrier. In general, it is preferable to administer the pharmaceutical composition in orally-administrable form, but certain formulations are preferably administered via a parenteral, intravenous, intramuscular, transdermal, buccal, subcutaneous or suppository route. Intravenous formulations are preferably administered in sterile saline. Of course, one of ordinary skill in the art may modify the formualtions within the teachings of the specification to provide numerous formulations without rendering the compositions of the present invention unstable or compromising their therapeutic activity.

The amount of agent included within therapeutically active formulations according to the present invention is an effective amount for treating the infection or condition. In general, this amount usually ranges from less than about 1 mg. to about 500 mg. or more, depending upon the condition or infection treated and the route of administration. Administration of the active agent may range from continuous (intravenous drip) to several oral administrations per day (for example, Q.I.D.) and may include oral, topical, parenteral, intramuscular, intravenous, sub-cutaneous, buccal and suppository administration, among other routes of administration.

To prepare the pharmaceutical compositions according to the present invention, one or more of the compositions of the present invention is intimately admixed with a pharmaceutically acceptable carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, manitol, lactose and related carriers, diluents, granulating agents, lubricants, binders, disintegrating agents and the like may be used. If desired, the tablets or capsules may be enteric-coated by standard techniques. The compositions according to the present invention may also be administered topically, especially for treating certain Herpes infections. Topical formulations may include a salve or cream base.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

In particularly preferred embodiments according to the present invention, the compounds and compositions may be used to treat viral infections of mammals and in particular humans. They will be of particular use in the treatment of viral infections caused by the envelope viruses, and in particular, HSV (I and II), EBV, CMV, VZV and HIV. Generally, the compositions will be administered orally in amounts ranging from about 1 to about 500 mg. or more up to four times a day. These compositions are preferably administered orally, but may be administered parenterally, topically or in suppository form. Topical formulations are especially preferred for treating Herpes infections.

The compositions of the present invention may also be used prophylactically to prevent infection or to prevent the occurrence of clinical symptoms associated with the viral infection. Thus, the present invention also encompasses methods for the therapeutic or prophylactic treatment of viral infections, and in particular Herpes and HIV infections, comprising administering to a patient in need of such treatment an amount of a compound according to the invention effective for alleviating, and/or preventing the viral infection. In the prophylactic treatment according to the present invention, it is preferred that the antiviral composition utilized should be as low in toxicity and preferably non-toxic to the patient. It is particularly preferred in this aspect of the present invention that the composition which is used should be maximally effective against the virus and should exhibit a minimum of toxicity to the patient.

In addition, compositions according to the present invention may be administered alone or in combination with other agents, especially including other agents of the present invention. In particularly preferred compositions utilizing a combination of agents according to the present invention, one (or more) of the compositions of Group III which exhibit activity as biological modifiers is coadministered in a biological modifier effective amount in combination with a therapeutically effective amount of a second biologically active compound. Compositions according to this aspect of the present invention are effective for enhancing the biological activity of certain agents according to the present invention by reducing the metabolism or inactivation of these agents.

In a particularly preferred pharmaceutical composition and method for treating herpes and especially HSV I and II infections, an effective amount of 1-(2-deoxyribofuranosyl)-5-ethyl-2-pyrazinone-4-N-oxide or 1-(2-deoxyribofuranosyl)-5-methyl-2-pyrazinone-4-N-oxide is administered to a patient suffering from such an infection or infections to alleviate the symptoms of such infections.

The present invention is now described, purely by way of illustration, in the following examples. It will be understood by one of ordinary skill in the art that these examples are in no way limiting and that variations of detail can be made without departing from the spirit and scope of the present invention.

I. Chemical Synthesis of
5-Substituted-2-Pyrazinone-4-N-oxidenucleosides

In general these compositions may be synthesized according to the general method of chemical synthesis described hereinabove. In the case of compositions in which the 5 substituent is a hydrogen or an unsubstituted alkyl group ranging in size from $C_1$ to $C_3$, i.e. a $CH_3$, $CH_2CH_3$, $CH_2CH_2CH_3$ or i-propyl group, or a benzyl group, the 5-substituted-2-pyrazinone-4-N-oxide (as its protected form) is generally first synthesized and then the substituted base subsequently is condensed with a blocked sugar synthon (2-deoxyribose) to produce, after deprotection, the 5-substituted-2-pyrazinone-4-N-oxide-2'-deoxynucleosides. Compositions according to the present invention in which the 5-substituent is an H or $CH_3$ may be synthesized according to literature preparations. (See, Berkowitz and Bardos, *J. Med. Chem.*, 16, 183 (1973) and Bobek and Bloch, *J. Med. Chem.*, 20, 458 (1977)).

Melting points were determined using a MelTemp apparatus and are uncorrected. Proton NMR spectra were recorded on a Varian T-60 or EM390 instrument and reported as ppm (δ) downfield from $(CH_3)_4Si$. Infrared spectra were obtained using a MattsonPolaris FT-IR spectrophotometer; absorbances reported reflect only the strongest bands recorded or tentatively-assigned bands relevant to the structure determination. Ultraviolet spectra were recorded on a Cary model 118C spectrophotometer. Analytical thin-layer chromotography (TLC) was done using Analtech silica gel GHLF Uniplates. Flash-column chromatography employed Baker silica gel.

EXAMPLE 1

1-(2-Deoxy-B - D-ribofuranosyl)-5-ethyl-2-pyrazinone-4-N-oxide

2-Amino-5-ethylpyrazine, prepared by the method described by Pitre and Boveri, *Chem. Ber.*, 100, 560 (1967) in acetic was converted by diazotization with sodium nitrite (added dropwise) over a period of about 20 minutes (See Scheme I). The mixture was stirred at room temperature for approximately 1.5-2 hr, until the starting material could no longer be detected (TLC in EtOAc). This mixture was neutralized to pH 7.0 which was followed by ethyl acetate extraction (6X), drying (MgSO$_4$) of the extract and concentration under reduced pressure to an oily residue. The crude intermediate, 2-hydroxy-5-ethylpyrazine, was co-evaporated with dry benzene to ensure removal of moisture, then dissolved in anhydrous pyridine and treated dropwise with benzoyl chloride followed by overnight stirring (15 hr followed by TLC in 10% EtOAc/CH$_2$Cl$_2$) at ambient temperature to give, after isolation by dissolving in cold water followed by extraction (toluene) followed by flash chromatography (Silica gel, 10% EtOAc/CH$_2$Cl$_2$), followed by recrystallization CH$_2$Cl$_2$/EtOAc, 48.8% overall yield of the analytically pure 0-benzoyl derivative, mp 34° C. (2, see scheme I).

The 0-benzoyl derivative 2 in anhydrous dichloroethane at 0° C. was converted to the N-oxide by adding m-chloroperbenzoic acid (1.3 molar excess) in small portions. The resulting solution was stirred at 60°-65° C. for 12-15 hrs. The reaction mixture was diluted with 20ml of CH$_2$Cl$_2$ followed by column chromatography (1:10 ethyl acetate/CH$_2$Cl$_2$), gave the N-oxide derivative (3) in 81% yield as a white solid recrystallized from CH$_2$Cl$_2$/ethyl acetate, m.p. 78° C. The 0-benzoyl group was de-protected in NaOMe in MeOH (by dropwise addition of 2N NaOMe) at 5° C. for 1 hour followed by stirring at room temperature for 1 hour. TLC (1:10 ethyl acetate/CH$_2$Cl$_2$) indicated complete de-protection after 1 hour. The reaction solution was then neutralized with Dowex 50 (H+ form) ion exchange resin which was washed with methanol. Concentration of the filtrates gave a solid product which was washed with n-hexane and recrystallized from methanol to yield 1,2-dihydro-5-ethyl-2-pyrazinone-4-N-oxide (4), m.p. 211° C. (dec.) in about 65% yield.

The pyrazine base (4) was then silylated in a mixture of chlorotrimethylsilane (about 1.1 moles based upon 4) and hexamethyldisilazane (about 2 moles based upon 4) by refluxing under dry conditions for 40 minutes. The resulting solution was concentrated under reduced pressure and twice coevaporated with dichloroethane to remove all traces of hexamethyldisilazane. The residue was then dissolved in dry dichloroethane, cooled to 0° C. To that solution were added consecutively, mercuric oxide (about 1.1 moles based upon 4), mercuric bromide (about 1.05 moles based upon 4) and 2-deoxy-3,5-di-0-p-chlorobenzoyl-alpha-D-ribofuranosyl chloride (about 1.6 moles based upon 4) obtained by the method described by Fox, et al., *J. Amer. Chem. Soc.*, 83, 4066 (1966) and Kotick, et al., *J. Oro. Chem.*, 34, 3806 (1969)). The slurry was stirred at 0°-5° C. for about 30 minutes, then at room temperature for 15 minutes. The suspension was filtered, the salts washed with CH$_2$Cl$_2$, and the filtrates washed by extraction twice with 30% aqueous KI and twice with water (dried Mg$_2$SO$_4$) and concentrated to a multi-component residue. This residue was flash-chromatographed first with 30% ethyl acetate/methylene chloride to give the anomeric blocked nucleosides (5, alpha and beta). The alpha anomer was separated from the beta anomer by a second flash chromatography (30% ethyl acetate/methylene chloride, alpha anomer came off the column after the beta anomer) and recrystallized from methylene chloride in about 31% yield (m.p. 129°-130° C.). The beta anomer was separated and recrystallized from methylene chloride in 43.8% yield (m.p. 142° C.).

The beta anomer of 5 was dissolved in cold anhydrous methanol presaturated with dry ammonia, sealed and stirred at 4° C. for 3 hours, then concentrated to dryness under reduced pressure at room temperature. The residue was washed thoroughly with ether, then dried under vacuum to obtain crude 6; an additional amount of 6 was obtained by preparative thin-layer chromatography of the ether washings using 10% methanol/CH$_2$Cl$_2$. Recrystallization of the combined portions from methanol/ether and a final washing with ether yielded 81% of pure 1-(2-Deoxy-B-D-ribofuranosyl)-5-ethyl-2-pyrazinone-4-N-oxide 6 having a melting point of 162°-164° C. $^1$HNMR (CD$_3$OD) 1.25 (t, 3H, —CH$_2$CH$_3$), 2.7 (q, 2H, —CH$_2$CH$_3$), 2.2–2.6 (m, 2H, 2'-H), 3.81–3.98 (m, 2H, 5'-H), 4.01–4.18 (m, 1H, 4'-H), 4.41–4.58 (m, 1H, 3'-H), 6.41 (t, 2H, 1'-H), 7.7 (s, 1H, C$^6$-H), 8.3 (s, 1H, C$^3$-H). IR (KBr) 3384, 3355 (OH), 2927, 1671 (C=O), 1617 (C=C), 1472, 1436, 1317, 1231 (N->0), 1191, 1104, 877 (m, N->0) cm-1 UV (CH30H) 215, 284, 345 nm.

EXAMPLE 2

1-(2-Deoxy B-D-ribofuranosyl)-5-propyl-, -5-i-propyl- or -5-benzyl- 2-pyrazinone-4-N-oxide These compositions are synthesized by the method employed in example 1. 5-propyl-, 5-isopropyl- and 5-benzyl- 2-pyrazinone-4-N-oxide are first synthesized and are subsequently condensed with the protected deoxyribose sugar in the same manner as described for example 1.

5-propyl-2-pyrazinone-4-N-oxide is first synthesized by condensing equimolar amounts of methyl dimethoxyacetate and methyl butyrate in the presence of 1 equivalent of sodium methoxide in dry benzene at reflux for about 3-4 hours (See scheme II). The cooled solution is subsequently poured into cold 50% acetic acid, separated and the aqueous portion is extracted with ether (3X). Organic extracts are washed with saturated sodium bicarbonate, dried and concentrated to yield 2-ethyl-4,4-dimethoxyacetoacetate (7). Compound 7 is subsequently decarboxylated by reflux in a mixture of methanol and 2N KOH solution for 1 hour to produce propylglyoxal dimethylacetal 8, which is isolated by partition of the reaction mixture between water and ether and concentration of the organic mixture. Compound 8 is hydrolyzed in a 3% H$_2$SO$_4$ solution by refluxing for 1 hour. The hydrolyzed in a 3% H$_2$SO$_4$ solution by refluxing reaction mixture is subsequently allowed to cool to 5 C and is carefully neutralized with NaHCO$_3$. The aqueous solution of propylglyoxal is then added to a solution of aminoacetamidine dihydrobromide (1 eq., prepared by the method of Mengelberg, *Chem. Ber.*, 89, 1185 (1956)) in methanol at −35° to −40° C. A solution of sodium hydroxide (12.5N) representing about 3.5-4 equivalents is added slowly so that the temperature of the reaction mixture is maintained below about −35° C. 30 minutes after completing the addition of sodium hydroxide, the reaction is allowed to warm to room temperature, stirred for several hours, acidified with HCl to pH 6 and concentrated in vacuo. The resulting residue is then partitioned between water and ethyl acetate (3X), the organic layer is decolorized with charcoal, dried and concentrated to produce 2-amino-5-propylpyrazine 9 which is recrystallized from n-hexane. Compound 9 is diazotised in 50% acetic acid by the slow addition of NaNO$_2$ in 50% acetic acid at 0°-5° C. followed by holding the reaction at room temperature for 1-3 hours. Cautious neutralization of this solution with 4 NaOH is followed by ethyl acetate extraction and isolation of a crude residue which is co-evaporated with benzene to an anhydrous state, dissolved in pyridine and benzoylated (excess benzoyl chloride in pyridine) to yield, after workup and chromatography, 2-benzyloxy-5-propylpyrazine 10. Compound 10 is subsequently oxidized with m-chloroperbenzoic acid in dichloroethane as described in Example 1, hereinabove, to give 2-benzyloxy-4-oxo-5-propyl-pyrazine 11. Compound 11 is debenzoylated in sodium methoxide/methanol using conventional workup procedures to produce 1,2-dihydro-5-propyl-2-pyrazinone-4-N-oxide 12. Compound 12 is then silylated as described in example 1, above and coupled to 2-deoxy-3,5-di-0-p-chlorobenzoyl-alpha-D-ribofuranosyl chloride, also as described above. The anomeric blocked 2'-deoxyriboside of 5-propyl-2-pyrazinone-4-N-oxide is then separated, recrystallized and deprotected in a fashion analogous to the 5-ethyl derivative as described above to produce 1-(2-Deoxy-B-D-ribofuranosyl)-5-propyl-2-pyrazinone-4-N-oxide 13.

To synthesize 1-(2-Deoxy-B-D-ribofuranosyl)-5-i-propyl-or -5-benzyl- 2-pyrazinone-4-N-oxide, the analogous procedure used to synthesize the 5-propyl derivative is used. In the case of the 5-i-propyl and 5-benzyl derivatives, 5-i-propyl and 5-benzyl-2-pyrazinone-4-N-oxide are synthesized using methyl isobutyrate and methylphenylacetate respectively, in place of methyl butyrate in the preceding scheme. All other steps in the syntheses are analogous to those for the 5-propyl derivative.

EXAMPLE 3

1-(2-Deoxy-B-D ribofuranosyl)-5-iodo- and -5-bromo-2-pyrazinone-4-N-oxide

Commercially available 2-chloropyrazine (Aldrich Chemicals, Milwaukee, Wis. U.S.A.) in 1,2-dichloroethane is treated portionwise with a 60% molar excess of m-chlorperbenzoic acid at 0° C., then warmed to 60° C. for approximately 15 hours. The organic solution is then allowed to cool to room temperature, washed with aqueous $NaHCO_3$, then with water and then dried and concentrated. Chromatographic separation yields 2-chloropyrazine-4-oxide (14) in 70-80% yield (See scheme III).

Compound 14 is hydrolyzed by refluxing with aqueous NaOH (1.3 N) for 2 hours, followed by acidification with 5N HCl, neutralization with 6N NaOH and evaporation to dryness. The solid residue is extracted (3X) in hot ethanol which, upon concentration, yields 2-pyrazinone-4-N-oxide (15) in about 50-60% yield (m.p. 300° C.). A solution of compound 15 in dry pyridine is treated dropwise with a 20% molar excess of benzoyl chloride and the resulting solution stirred overnight with exclusion of moisture. Subsequent hydrolysis of the reaction mixture in ice water yields a precipitate of 2-benzyloxy-4-N-oxopyrazine (16) which is filtered, washed with 10% $NaHCO_3$, and then cold water and then subsequently is dried. The crude product is suspended in n-hexane and re-filtered to improve the purity.

Compound 16 and a slight molar excess of mercuric acetate are dissolved in 0.1 M (pH 6.0) sodium acetate buffer and warmed to 50 C for 15 hours. After cooling, the precipitated mercuri derivative is washed with 0.16N NaCl and with ethanol and dried in vacuo. This crude intermediate is then dissolved in 0.05M KI and treated with a 50% aqueous ethanol solution of $I_2$ at room temperature for 1 hour. Chloroform extraction of the reaction mixture followed by chromatographic purification yields the synthetic intermediate 2-benzyloxy-5-iodo-4-oxopyrazine (17a). The benzyloxy group is removed in methanolic ammonia to produce the 1,2-dihydro-5-iodo-4-N-oxide (17).

Compound 17 is silylated in a mixture of chlorotrimethylsilane and hexamethyldisilazane as described in Example 1, above and condensed with 2-deoxy-3,5-di-0-p-chlorobenzoyl-alpha-D-ribofuranosyl chloride in mercuric oxide and mercuric bromide. Chromatographic separation of the blocked anomeric compounds 18 followed by de-protection in methanolic ammonia results in 1-(2-Deoxy-B-D-ribofuranosyl)-5-iodo-2-pyrazinone-4-N-oxide (19).

The 5-bromo- derivative is synthesized analogously to the 5-iodo derivative except that $Br_2$ is used in place of $I_2$ during the 5-halogenation step described above.

EXAMPLE 4

1-(2-Deoxy-B-D-ribofuranosyl)-5-ethynyl, -5-propynyl and -5-phenylethynyl-2-pyrazinone-4-N-oxide 2-benzoyloxy-5-iodo-4-oxopyrazine (prepared according to Example 3) is dissolved in dry, degassed triethylamine and treated with a 20% molar excess of trimethylsilylacetylene, 2.5 mole % of CuI and 1 mole % of bis(triphenylphosphine)$PdCl_2$ under nitrogen at room temperature for 3 days (See Scheme IV). Dilution to 4 times the original volume with THF, filtration under $N_2$ and concentration of the filtrate gives a residue which is crystallized from anhydrous methanol to yield 2-benzoyloxy-5-(trimethylsilylethynyl)-4-oxopyrazine (20). Compound 20 is then dissolved in an anhydrous saturated methanolic ammonia solution at 0° C., sealed and kept at 0°-5° C. for 20 hours. The resulting solution is then concentrated in vacuo, crystallized from acetone, filtered and dried to yield 1,2-dihydro-5-ethynyl-2-pyrazinone-4-N-oxide (21).

Compound 21 is refluxed in an excess of hexamethyldisilazane and minor amount of trimethylsilyl chloride for three hours, concentrated in vacuo and co-evaporated twice with 1,2-dichloroethane to remove any residual hexamethyldisilazane. The residue is dissolved in anhydrous dichloroethane and added to an ice-cooled solution of 2-deoxy-3,5-di-0-p-chlorobenzoyl-alpha-D-ribofuranosyl chloride in dichloroethane. The resulting solution is treated with a dichloroethane solution of $SnCl_4$ and stirred at 0° C. for 2 hours or until reaction completion is indicated by TLC. The solution is then diluted with dichloroethane and aqueous $NaHCO_3$. The mixture is then filtered, the organic solution washed with water and then concentrated to a mixture of the anomeric blocked 2'-deoxyriboside of 5-ethynyl-2-pyrazinone-4-N-oxide (22) which is then separated (chromatography), recrystallized and de-protected in a fashion analogous to the 5-ethyl derivative as described above to produce 1-(2'-Deoxy-B-D-ribofuranosyl)-5-ethynyl-2-pyrazinone-4-N-oxide 23.

The 5-propynyl- and 5-phenylethynyl- derivatives are synthesized by an analogous method, with the exception that propylene and phenylacetylene are used to introduce the indicated substituents at the 5 position of 2-benzoyloxy-5-iodo-4-oxopyrazine (17a). All other steps are performed analogously to the 5-ethynyl chemical synthesis. These compositions may also be synthesized from 1-(2-deoxy-B-D-ribofuranosyl)-2-pyrazinone-4-N-oxide by first iodinating and then displacing the 5-iodo group using the above-described procedure.

EXAMPLE 5

1-(2-Deoxy-B-D-ribofuranosyl)-5-bromovinyl-2-pyrazinone-4-N-oxide 2-amino-4-oxopyrazine is dissolved in 0.1 M sodium acetate buffer (pH 6.0) at a concentration of 0.02 M. An equal volume of 0.10 mercuric acetate in the same buffer is added and the mixture heated at 50° C. for 3 hours or until TLC indicates consumption of the starting material (See scheme V). The solution is then cooled and the precipitated product collected and washed twice, successively with 0.2N NaCl followed by ethanol. The product is dried in vacuo and used without further purification. The crude mercurated pyrazine oxide is dissolved/suspended in 0.05M KI and treated with a 50% aqueous-ethanolic solution of I$_2$ and stirred for 1 hr. at room temperature. The aqueous reaction mixture is then extracted with chloroform and the extracts concentrated and chromatographically purified, to give 2-amino-5-iodo-4-oxopyrazine (24) See Dale, et al., Biochemistry, 14, 2447 (1975).

Compound 24, 2.5 molar equivalents of methyl acrylate, a catalytic quantity of palladium diacetate in acetonitrile and an excess (2.2 mole %) of triethylamine are refluxed under anhydrous conditions for 12 hours or until TLC evidences only one major product and no starting material (24) remaining. The reaction mixture is thereafter concentrated and recrystallized from hot methanol, to yield 2-amino-5-((methoxycarbonyl)ethenyl)-2-oxopyrazine (25). Compound 25 is dissolved in 50% aqueous acetic acid, then treated portionwise with NaNO$_2$ at 0° C., then warmed at 70° C. for 4 hours. The precipitated 2-oxo-derivative is then suspended and stirred in 0.5N KOH until TLC evidences full conversion to 2-hydroxy-5-(carboxylethenyl)-4-oxopyrazine potassium salt (26) which is crystallized upon cooling and partial concentration, or as the acid form, upon acidification with 1N HCl.

Compound 26 is then benzoylated with benzoyl chloride in pyridine under standard conditions to give 2-benzoyloxy-5-(2-(carboxyethenyl))-4-oxopyrazine (27). Compound 27 is dissolved in a solution of 0.1 equivalents of KOAc in hot water and treated portionwise with a 5% molar excess of N-bromosuccinimide, then heated from 1 hour or until TLC shows completion of the conversion to 2-benzoyloxy-5-(2-bromovinyl)-4-oxopyrazine (28), which is precipitated by ice-cooling of the completed reaction, filtered, washed with water and recrystallized from methanol. Compound 28 is debenzoylated by treatment with cold saturated anhydrous ammonia in methanol at 0°–5° C. followed by concentration in vacuo and washing the residue with ether to remove benzamide from the product 1,2-dihydro-5-(2-bromovinyl)-4-oxopyrazine, compound 29.

Compound 25 is silylated and condensed with 1-(3,5-di-0-(p-chlorobenzoyl)-2-deoxy-alpha-D-ribofuranosyl chloride, under catalysis of 1 molar equivalent of HgO and HgBr2 in dichloroethane according to the procedure set forth in example 1. The anomeric mixture of alpha and beta 1-(2-deoxy-3,5-di-0-(p-chlorobenzoyl)-D-ribofuranosyl)-5-(bromovinyl)-4-oxopyrazin-2-ones, are separated by chromatography and crystallized to give the desired beta-anomer 30. Compound 30 is deprotected by treatment with a cold, saturated, anhydrous solution of methanolic ammonia, followed by concentration and trituration with ether to give a filterable precipitate 1-(2-deoxyribofuranosyl)-5-bromovinyl-2-pyrazinone-4-N-oxide 31.

EXAMPLE 6

1-(2-Deoxy-B-D-ribofuranosyl)-5-vinyl-2-pyrazinone-4-N-oxide 2-benzyloxy-5-iodo-4-oxopyrazine (17) obtained from the synthesis in Example 3, a twofold molar excess of triethylamine, a catalytic amount of diaceto-bis(triphenylphosphine) palladium in excess vinyl acetate are heated in a sealed tube at 100° C. for 5 hours according to the general method of Arai and Daves, Jr., *J. Heterocyclic Chem.*, 15, 351 (1978) (See scheme VI). The cooled mixture is then partitioned between chloroform and water and the chloroform soluble portion is chromatographed on silica gel to give 5-benzyloxy-5-vinyl-4-oxopyrazine (32), which is then deprotected with methanolic ammonia at 0.C followed by concentration in vacuo and washing the residue with ether to remove benzamide from the product 1,2-dihydro-5-vinyl-4-oxopyrazine, compound 33.

Compound 33 is then silylated and condensed with 1-(3,5-di-0-(p-chlorobenzoyl)-2-deoxy-alpha-D-ribofuranosyl chloride, under catalysis of 1 molar equivalent of HgO and HgBr$_2$ in dichloroethane according to the procedure set forth in example 1. The anomeric mixture of alpha and beta 1-(2-deoxy-3,5-di-0-(p-chlorobenzoyl)-D-ribofuranosyl)-5-(vinyl)-4-oxopyrazin-2-one, are separated by chromatography and crystallized to give the desired beta-anomer 34. Compound 34 is deprotected by treatment with a cold, saturated, anhydrous solution of methanolic ammonia, followed by concentration and trituration with ether to give 1-(2-deoxy-B-D-ribofuranosyl)-5-vinyl-2-pyrazinone-4-N-oxide 35.

EXAMPLE 7

1-(2 Deoxy B D ribofuranosyl)-5-trifluoromethyl-2-pyrazinone-4-N-oxide 4-oxopyrazine-2-one is formylated (formaldehyde, aqueous base) to produce 5-hydroxymethyl-4-oxopyrazine-2-one (35a) according to the procedure of Scheit, Chem. Ber., 99, 3884-3891 (1966). Compound 35 is subsequently oxidized to the 5-carboxylic acid derivative (36) following, generally, the procedure set form in Imai and Honjo, *Chem. Pharm. Bull.*, 13, 7 (1965). Thereafter, the 5-carboxylic acid (36) is treated with sulfur tetrafluoride to produce the 5-trifluoromethyl-2-pyrazinone-4-N-oxide (37) by the method described by Mertes and Sahes, *J. Pharm. Sci.*, 52, 508 (1963). Compound 37 is subsequently condensed with 1-(3,5-di-0-(p-chlorobenzoyl)-2-deoxy-alpha-D-ribofuranosyl chloride, under catalysis of 1 molar equivalent of HgO and HgBr$_2$ in dichloroethane according to the procedure set forth in example 1, above. The anomeric mixture of alpha and beta 1-(2-deoxy-3,5-di0-(p-chlorobenzoyl)-D-ribofuranosyl)-5-trifluoromethyl-2-pyrazinone-4-N-oxide, is separated by chromatography and crystallized to give the desired beta-anomer 38. Compound 38 is deprotected by treatment with a cold, saturated, anhydrous solution of methanolic ammonia, followed by concentration and trituration to yield 1-(2-deoxy-B-D-ribofuranosyl)-5-trifluoromethyl-pyrazinone-4-N-oxide 39.

Alternatively, 4-oxopyrazin-2-one-2'-deoxyriboside is first protected (tetraisopropyldisiloxanyl groups on the 3',5' OH positions or with alternative protecting groups), formylated in aqueous base and formaldehyde as above to produce the 5-hydroxymethyl derivative. The 5-hydroxymethyl (3' and 5'OH groups) derivative is protected and then subsequently oxidized to the 5-carboxylic acid which is subsequently fluorinated and deprotected.

As another alternative, 5-vinyl-4-oxopyrazine-2-one, prepared according to Example 6, above is first subjected to a standard ozonolysis procedure to produce 5-formyl-4-oxopyrazine2-one (40). Compound 40 is subsequently oxidized to the 5-carboxylic acid derivative of 4-oxopyrazine-2-one which is subsequently fluorinated with sulfur tetrafluoride generally as described by Mertes and Sahes, supra and above and condensed according to the above-described procedures. Alternatively, 1-(2-deoxy-B-D-ribofuranosyl)-5-vinyl-2-pyrazinone-4-N-oxide is subjected to the same ozonolysis and oxidation procedures as described above.

EXAMPLE 8

1-(2-Deoxy-B-D-ribofuranosyl)-5-methylvinyl-, 5-phenylvinyl- and 5-diphenylvinyl2-pyrazinone-4-N-oxide 2-benzyloxy-5-iodo-4-oxopyrazine (17a), which is obtained from the synthesis in Example 3 is reacted with 1 equivalent of propene and 1 equivalent of triethylamine in a catalytic amount of palladium acetate and triphenyl phosphine at a temperature of approximately 100°–135° C. under inert gas (argon) for approximately 35–40 hours according to the general procedure described by Dieck and Heck, J. Amer. Chem. Soc., 96, 1134, (1974) and as set forth in scheme VIII. Thereafter, the reaction mixture is cooled and extracted with methylene chloride, placed on column chromatography and separated to provide the 2-benzoyloxy-5-methylvinyl-4-oxopyrazine, which is then de-protected with methanolic ammonia at 0° C. followed by concentration in vacuo and washing the residue with ether to remove benzamide from the product 5-methylvinyl-4-oxopyrazine-2-one, compound 41.

Compound 41 is then silylated and condensed with 1-(3,5-di-0-(p-chlorobenzoyl)-2-deoxy-alpha-D-ribofuranosyl chloride, under catalysis of HgO and HgBr$_2$ in dichloroethane according to the procedure set forth in examples 1 and the analogous example 12. The anomeric mixture of alpha and beta 1-(2-deoxy-3,5-di-0-(p-chlorobenzoyl)-D-ribofuranosyl)- 5-methylvinyl-4-oxopyrazin-2-one, are separated by chromatography and crystallized to give the desired beta-anomer 42. Compound 42 is deprotected by treatment with a cold, saturated, anhydrous solution of methanolic ammonia, followed by concentration and trituration with ether to give 5-methylvinyl-4-oxopyrazin-2-one-2,-deoxyriboside 43.

The corresponding 5-phenylvinyl- and 5-diphenylvinylderivatives are synthesized by analogous procedures except that 2-phenyl ethylene and 2,2-diphenyl ethylene are utilized to introduce the 5-phenylvinyl- and 5-diphenylvinyl derivatives, respectively before condensation with the blocked deoxyribose sugar.

EXAMPLE 9

1-(2,3-Dideoxy-2,3-didehydro-B-D-ribofuranosyl)-5-Substituted, 2-pyrazinone-4-N-oxide 1-0-methyl-3-0-trifluoromethylsulfonyl-5-0-(p-methoxytrityl)-2-deoxy-alpha-D-ribofuranose, prepared according to the general synthesis of Dvatkina and Azbayen, Synthesis, 961 (1984) with the exception that the p-methoxytrityl (acid labile) group replaces the benzoyl group (base labile), is subjected to t-BuO$^-$ K$+$ in DMSO followed by weak acid (to remove the group) and acylation (Ac$_2$O in pyridine) which results in the formation of the 1,5-di-0-acetyl-2,3-didehydroribofuranose derivative (44) (See scheme IX). The didehydro derivative 44 is condensed with the silylated 5-substituted 4-oxopyrazine-2-one as prepared hereinabove or as prepared according to the methods of Bobek and Bloch, J. Med. Chem., 20, 458 (1977) and Berkowitz, et al., J. Med. Chem., 16, 183 (1973) (5-CH3 or 5H -2-pyrazinone-4-N-oxide) in the presence of trimethylsilyltriflate (trimethylsilyltrifluoromethanesulfonate) according to the method of Chen, et al., J. Med. Chem., 33, 1555 (1990) and Greengrass et al., J. Med. Chem., 32, 618 (1989), separated into alpha and beta anomers, deprotected and crystallized to produce compound 45.

Alternatively, the corresponding 1-(2-deoxy-B-D-ribofuranosyl)-5-substituted-4-oxo-pyrazine-2-one, described in examples 1-17, above, and, in addition, 1-(2-deoxy-B-D-ribofuranosyl)-5-methyl-4-oxo-pyrazine-2-one and 1-(2-deoxy-B-D-ribofuranosyl)-4-oxo-pyrazine-2-one, prepared by the methods described by Bobek and Bloch, J. Med. Chem., 20, 458 (1977) and Berkowitz, et al., J. Med. Chem., 16, 183 (1973) are treated with Methoxytrityl chloride ((p-methoxyphenyl)-di-phenylmethyl chloride) in pyridine overnight or until TLC indicates complete conversion of the free 5'-OH group to the Methoxytrityl protected derivative (See, Greengrass, et al., J. Med. Chem., 32, 618 (1989)). This derivative is subsequently extracted and then crystallized or separated on column chromatograph (silica gel), dissolved in pyridine and treated with Mesyl chloride (methyl sulfonylchloride) to produce the (2-deoxy-5-0-methoxytrityl-3-0-mesyl-B-D-ribofuranosyl) derivative 44a.

Compound 44a is then treated with t-BuO$^-$ K$+$ in DMSO by standard procedure followed by removal of the methoxytrityl group to de-protect the 5'OH position by simple acid cleavage in formic acid/H$_2$O for about 1 hour to produce 1-(2,3-Dideoxy-2,3-didehydro-B-D-ribofuranosyl)-5-Substituted, 2-pyrazinone-4-N-oxide (Compound 45).

EXAMPLE 10

1-(2,3-Dideoxy-B-D-ribofuranosyl)-5-Substituted, 2-pyrazinone-4-N-oxide

The 2,3-dideoxyribofuranosyl sugar is first synthesized according to the method set forth by Okabe, et al., J. Org. Chem., 53, 4780 (1988) and then condensed utilizing standard procedures described hereinabove to produce the corresponding dideoxy nucleoside analog(s) according to scheme X.

L-glutamic acid is first treated with sodium nitrite in hydrochloric acid/water to produce the carboxylic acid lactone derivative(46). Compound 46 is then treated with dimethylborohydride in tetrahydrofuran to reduce the carboxylic acid to the corresponding alcohol (47), which is subsequently protected with tertiarybutyldimethylsilyl chloride in methylene chloride using imidazole as catalyst to produce the corresponding product 48. Protected lactone 48 is subsequently reduced to the corresponding 1-hydroxy derivative 49 which is separated and subsequently acetylated in acetic anhydride/triethylamine (16 hours, room temperature) to the corresponding 1-acetate 50. Compound 50 is thereafter condensed with 1,2-dihydro-5-substituted-2-pyrazinone (as prepared above, or, in the case of the 5-methyl and 4-oxo-pyrazine-2-one (5-H) as previously described) in which the 2-oxo position has first been silylated. The condensation method is as described by Chen, et al., J. Med. Chem., 33, 1555 (1990), and utilizes trimethylsilyltriflate in anhydrous 1,2-dichloroethane followed by extraction and column chromatography on silica gel which produces the alpha and beta anomers of the condensed product 51. The silyl protecting group is removed with tetra-n-butylammonium fluoride in tetrahydrofuran and the alpha and beta anomers are separated by column chromatography to provide the respective 1-(2',3-dideoxy-B-D-ribofuranosyl)-5-Substituted-2-pyrazinone-4-N-oxide.

EXAMPLE 11

1-(2-substituted, 2-deoxy- and 2,3-dideoxy-B-D-arabinofuranosyl)-5-Substituted, 2-pyrazinone-4-N-oxide In general, these compositions are produced by first synthesizing the known 2-substituted arabinose sugar(s) and condensing with the 5-substituted-2-pyrazinone-4-N-oxide bases as is performed analogously herein.

Protected 1-0-acetyl-2-deoxy-2-alpha-substituted-arabinofuranose compound(s) (52), obtained by the method(s) described in Reichmann, et al., Carbohydrate Res., 42, 233 (1975), Ritzmann, et al., Carbohydrate Res., 39, 22 (1975), Su, et al., Jour. Org. Chem., 46, 1790 (1981), Tann, et al., Jour. Org. Chem., 50, 369 (1985), Watanabe, J. Med. Chem., 22, 20, (1979), Bothwirk, et al., J. Med. Chem., 33, 179 (1990), Mansuri, et al., Tet. Letters. 32, 1287 (1991) and Watanabe, et al., J. Med. Chem., 26, 152 (1983), in methylene chloride is subjected to anhydrous HBr gas at 0° C. for approximately 20-30 minutes (See Watanabe, et al., J. Med. Chem., 26, 154 (1983)) and the mixture is sealed and stored overnight at 4° C. In the case of the 1-0-acetyl-2-deoxy-2-alpha-amino-arabinofuranose, the 2-azido derivative is reduced with Pd/C and H2 and the resulting amino group is protected with a trimethylsilyl group in triethylamine. Solvent is thereafter removed at a temperature lower than about 35° C., the remaining acetic acid being removed by coevaporation with toluene. This produces the 1-bromo-2-deoxy-2-alpha-substituted arabinose compound(s) (53) as set forth in scheme XI.

The corresponding silylated 1,2-dihydro-5-substituted-2-pyrazinone (as prepared above, or, in the case of the 5-methyl and 4-oxo-pyrazine-2-one (5-H), as previously described by Bobek and Bloch and Berkowitz, et al., supra) in which the 2-oxo position has first been silylated, is condensed with 1-bromo-2-deoxy2-alpha-substituted arabinofuranose 53 by stirring the two compounds for several days (followed by TLC) in methylene chloride. The reaction is thereafter diluted with methylene chlorde, and then treated with methanol, filtered, washed with water and dried. The resulting condensed product is chromotographed to separate the alpha and beta anomers. The blocked beta anomer 54 is subsequently recrystallized after separation or obtained as a foam. The blocked beta anomer is thereafter treated with anhydrous methanolic ammonia to remove the hydroxyl protecting groups and the resulting product recrystallized to produce 1-(2-deoxy-2-substituted-B-D-arabinofuranosyl)-5-substituted-2-pyrazinone-4-N-oxide (55).

The corresponding 1-(2-substituted, 2,3-dideoxy-B-D-arabinofuranosyl)-5-Substituted, 2-pyrazinone-4-N-oxides are synthesized by an analogous method to that described above, except that the 1-0-acetyl-2-deoxy-2-alpha-substituted-3-deoxyarabinofuranose compound(s) are utilized in an analogous synthetic scheme as set forth above. Likewise, substitution of a fluoro at the 3 position of the sugar may also be performed. The substituted sugars are synthesized by methods analogous to those described above.

EXAMPLE 12

1-(3-substituted-2-deoxy-B-D-ribofuranosyl)- and 1-(3-substituted-B-D-ribofuranosyl) -5-Substituted, 2-pyrazinone 4-N-oxide 1-0-methyl-3-0-trifluoromethylsulfonyl-5-0-p-methoxybenzoyl-2-deoxy-D-threo-ribofuranoside prepared by the method of Dvatkina and Azbayen, Synthesis, 961 (1984) (56) is treated with lithium azide, lithium fluoride, lithium chloride or lithium iodide to produce the 1-0-methyl-3-substituted-5-0-p-methoxybenzoyl-2-deoxy-D-erythro-ribofuranoside (57) (See scheme XII). The 3-amino derivative (58) is produced by reducing the 3'-azido derivative in the presence of palladium catalyst and H2, which is subsequently silylated with trimethylsilylchloride in triethylamine to produce compound 59. The 3-CH2OH derivative (60) is produced by treating compound 56 with sodium cyanide or alternatively, tetraethylammonium cyanide to produce the 3'-cyano derivative (60) which is subsequently treated stepwise with potassium hydroxide and the borohydride reducing agent, B2H6 in THF to produce the 3-CH2OH derivative which is silylated in trimethylsilylchloride in triethylamine to produce the 3-CH2OHcontaining silyl-protected sugar 61.

The 1-0-methyl-3-substituted-5-0-protected (with benzoyl or trimethylsilyl groups)-2-deoxyribofuranoside (57. 59 or 61) is condensed with the corresponding silylated 1,2-dihydro-5-substituted-2-pyrazinone (as prepared above, or, in the case of the 5-methyl and 4-oxopyrazine-2-one (5-H), as previously described by Bobek and Bloch and Berkowitz, et al., supra) using the condensation method as described by Chen, et al., supra, which utilizes trimethylsilyltriflate in anhydrous 1,2-dichloroethane. The condensed product is subsequently extracted and separated by column chromatography on silica gel which produces the protected alpha and beta anomers of the condensed product, which upon exposure to methanolic ammonia, followed by workup and recrystallization produces 1-(3-substituted-2-deoxy-B-D-ribofuranosyl)-5-Substituted, 2-pyrazinone-4-N-oxide(62).

The corresponding 1-(3-substituted-B-D-ribofuranosyl)-5-substituted, 2-pyrazinone-4-N-oxide derivatives (2 position is substituted with OH) are synthesized in an analogous fashion from the corresponding 1-0-methyl-2-0-p-methoxybenzoyl-3-0-trifluoromethylsulfonyl-5-0-p-methoxybenzoyl-D-threoribofuranoside. All steps are analogous to those described above; protecting groups used on the 5-OH position of the sugar are identical to those used on 2-OH position, de-protection is same for 5-OH.

EXAMPLE 13

1 (4-substituted-B-D ribofuranosyl)- and 1-(4-substituted-2-deoxy-B-D-ribofuranosyl)-5 Substituted- 2-pyrazinone-4-N-oxide 1-0-methyl-2,3-isopropylidene-4,5-didehydroribofuranoside (63), obtained according to the method of Hugh and Otter, Chem. Commun., 173 (1966) is treated with $IN_3$, IF, ICl, or ICN under standard conditions to produce the 1-0-methyl-2,3-isopropylidene-4-substituted-5-iodo-ribofuranoside (64)(See scheme XIII). Compound 64 is then treated with lithium benzoate to displace the iodo group at the 5 position of the sugar resulting in 1-0-methyl-2,3-isopropylidene-4-substituted-5-0-benzoylribofuranoside (65). In the case of the 4-$CH_2OH$ and 4-$NH_2$ substitutents, these are produced by conversion of the 4-CN and 4-$N_3$ groups respectively. The 4-$CH_2OH$ derivative (66) is produced by treating the 4-CN derivative stepwise with potassium hydroxide and the borohydride reducing agent, $B_2H_6$ in THF to produce the 4-$CH_2OH$ derivative. In the case of the 4-$NH_2$ derivative (67), this compound is produced by simple reduction (Pd/$H_2$) of the 4-$N_3$ derivative. Compound 65, 66 or 67 is subsequently subjected to acid hydrolysis of the isopropylidene group (formic acid/water) followed by protection of the hydroxyl (and NH2) groups with acetic anhydride or benzoyl chloride to produce the corresponding 1-0-acetyl-2,3-0-acetyl-4-substituted-5-0-benzoyl-ribofuranoside (68) which is subsequently condensed with the corresponding silylated 1,2-dihydro-5-substituted-2-pyrazinone (as prepared above, or, in the case of the 5-methyl and 4-oxo-pyrazine-2-one (5-H), as previously described by Bobek and Bloch and Berkowitz, et al., supra) utilizing trimethylsilyltriflate in anhydrous 1,2dichloroethane as described by Chen, et al., supra and as used analogously, above to produce the alpha and beta anomers of the blocked ribonucleoside (69) which is subsequently separated on column chromatography, crystallized and de-blocked in methanolic ammonia to produce the 1-(4-substituted-B-D-ribofuranosyl)-5-substituted-2-pyrazinone-4-N-oxide (70).

The 1-(4-substituted-2-deoxy-B-D-ribofuranosyl)-5-substituted-2-pyrazinone-4-N-oxide is synthesized by a method analogous to that for 1-(4-substituted-B-D-ribofuranosyl)-5-substituted-2-pyrazinone-4-N-oxide which is described above, except that the starting protected ribofuranoside 1-0-methyl-2-deoxy-3-protected-4,5-didehydro-ribofuranoside, is first synthesized by the general method established by Hugh and Otter, supra starting from the 1-0-methyl-2-deoxy-3-protected-4,5-didehydroribofuranoside which is prepared according to the general literature preparation. The 2,-alpha-F substituted derivative is synthesized pursuant to the same general method starting from 1-0-methyl-2-deoxy-2-alpha-fluoro-3-protected-4,5-didehydroribofuranoside.

II. Synthesis of Substituted-Acyclo-5-Substituted2 pyrazinone-4-N-oxides

EXAMPLE 4

1-(acyclo-substituted)-5-Substituted-2-pyrazinone-4-N-oxide

These compositions are synthesized by the general method set forth in Scheme XIV. In general, the acyclo substituted analogs which are condensed onto the 5-substituted 2-pyrazinone4-N-oxide bases, are either purchased or are prepared from literature methods (Niedzwicki, et al., Biochem. Pharmacol., 31, 1857, 1982; Lin, et al., Nucleosides and Nucleotides, 9, 559, 1990; and Lin and Liu, J. Med. Chem., 28, 971, 1985). These compositions (71) are condensed with the corresponding silylated 1,2-dihydro-5-substituted-2-pyrazinone-4-N-oxide (as prepared above, or, in the case of the 5-methyl and 4-oxo-pyrazine-2-one (5-H), as previously described by Bobek and Bloch and Berkowitz, et al., supra) utilizing HgO/HgBr in refluxing solvent (condensation with chloro or bromo) or with trimethylsilyltriflate in anhydrous 1,2-dichloroethane as described by Chen, et al., supra and as used analogously above. The resulting composition is thereafter deprotected where required to produce 1-(acyclo-substituted)-5-substituted-2-pyrazinone-4-N-oxide (72).

In the case of 1-(acyclo-substituted)- 5-benzyl or (m-benzyloxybenzyl) benzyloxybenzyl) -2-pyrazinone-4-N-oxide, these compositions are synthesized by the coupling procedure described above wherein 1,2-dihydro-5- benzyl or (m-benzyloxybenzyl)-2-pyrazinone-4-N-oxide is first prepared (scheme XV) and then coupled onto the acyclo substituted analogs according to scheme XIV. In this scheme, condensation of the 1,2-dicarbonyl compound (73) with alpha-aminoacetamide gives the corresponding hydroxypyrazine derivative (74) (See Karmas and Spoerri, Jour. Amer. Chem. Soc., 74, 1580, 1952). The free hydroxyl group is then protected with a benzoyl group using benzoyl chloride in pyridine to produce benzoylated composition (75). Compound 75 is then oxidized to the 4-N-oxide derivative (76) with m-chloroperbenzoic acid in dichloroethane as described in several of the above examples. The 2-0-benzoyl group is subsequently removed in NaO-Me/MeOH and neutralized with Dowex (H+) ion exchange resin to produce the desired 5-(m-benzyloxybenzyl)-2-pyrazinone-4-N-oxide (77). Compound 77 is thereafter silylated and coupled to the substituted acyclo analog as indicated (chloro or bromo at condensing carbon) utilizing HgO/HgBr in refluxing solvent (benzene, xylene, toluene, acetonitrile, etc.) or alternatively using the 1-0Ac acyclo analog and condensed according to the method of Chen, et al., and as used analogously above.

EXAMPLE 15

1-(acyclo-substituted)-5-substituted-6- thiophenyl- or thiocyclohexyl- 2-pyrazinone-4-N-oxide These compositions are synthesized by the general method set forth in Scheme XVI. In general, the purchased or literature prepared compositions 71 as used in Example 14, above, in which hydroxyl or amine groups are protected (with the exception of the 1-0-acetyl group which is to be condensed with the 1-N of the pyrazinone base) are condensed with the corresponding silylated 1,2-dihydro-5-substituted-2-pyrazinone (as prepared above, or, in the case of the 5-methyl and 4-oxo-pyrazine-2-one (5-H), as previously described by Bobek and Bloch and Berkowitz, et al., supra) utilizing trimethylsilyltriflate in anhydrous 1,2-dichloroethane as described by Chen, et al., supra and as used analogously above, to produce 1-(acyclo-substituted)-5-substituted-2-pyrazinone-4-N-oxide (72).

In order to introduce a -S-Ph or -S-$C_6H_{11}$ group onto the 6-position of the 5-substituted pyrazinone base, compound(s) 72 is first treated with about 2.5 equivalents of lithium diisopropylamide (LDA) in tetrahydrofuran at −70° C. according to the method of Tanaka, et al., J. Med. Chem., 34, 1508 (1991), followed by reaction with either diphenyldisulfide or dicyclohexyldisulfide to produce 1-(acyclo-substituted)-5-substituted-6- thiophenyl- or thiocyclohexyl- 2-pyrazinone-4-N-oxide (78).

EXAMPLE 16

1-(acyclo- phenyl- or methyl-substituted)-5-methyl- or ethylsubstituted -6- thiophenyl- or thiocyclohexyl2-pyrazinone-4-N-oxide These compositions are synthesized by the general method set forth in Scheme XVII.

The purchased compositions benzyloxymethylchloride or ethoxymethylchloride (79) are condensed with the corresponding silylated 1,2-dihydro-5-methyl or ethyl -2-pyrazinone (as prepared in example 1 above, or, in the case of the 5-methyl-pyrazine-2-one-4-N-oxide, as previously described by Bobek and Bloch and Berkowitz, et al., supra) to produce 1-(acyclobenzyloxymethyl or methyl substituted)-5-methyl or ethyl substituted- 2-pyrazinone-4-N-oxide (80).

Compound 80 is subsequently treated as in example with about 2.5 equivalents of lithium di-isopropylamide (LDA) in tetrahydrofuran at −70° C. according to the, method of Tanaka, et al., J. Med. Chem., 34, 1508 (1991) as described for Example 15 followed by reaction with either diphenyldisulfide or dicyclohexyldisulfide to produce 1-(acyclo-substituted)-5-substituted-6- thiophenyl- or thiocyclohexyl- 2-pyrazinone-4-N-oxide (81).

Alternatively, the 5-methyl- or 5-ethyl- 2-pyrazinone-4-N-oxide derivative as prepared above can be treated according to the general method of Tanaka, et al., supra, as used above to introduce the thiophenyl or thiocyclohexyl group at the 6 position of the pyrazinone base. Subsequent condensation with benzyloxymethylchloride or ethoxymethylchloride or the corresponding 0-acetate results in compound 81.

III. Biological Activity

EXAMPLE 17

Anti-HSV Activity of 1-(2,-Deoxy-B-D-ribofuranosyl)-5-ethyl and -5-methyl-2-pyrazinone-4-N-oxide Antiviral (HSV) activities of 1-(2'-Deoxy-B-D-ribofuranosyl)-2-pyrazinone-4-N-oxide (A in table 1) and the corresponding 1-(2'-Deoxy-B-D-ribofuranosyl)-5-methyl-2-pyrazinone-N-oxide and 1-(2,-Deoxy-B-D-ribofuranosyl)-5-ethyl-2-pyrazinone-4-N-oxide (respectively, B and C of table 1) were determined according to the procedure described in Gao, et al., Antimic. Agents Chem., 34, 808 (1990), using the plaque reduction method. Table 1 indicates the relative antiviral activities of the three derivatives against HSV-1 (KOS strain).

TABLE 1

| Drug Concentration uM | Plaque Forming Units, % of Control | | |
|---|---|---|---|
| | A | B | C |
| 100 | 100 | 0.09 | 0.3 |
| 25 | 100 | 0.91 | 4.5 |
| 5 | 100 | 39.00 | 55.00 |
| 1 | 100 | 100.00 | 100.00 |

The date set forth in Table 1 evidences that composition A (5-H) is inactive, while both B and C exhibit significant antiherpes activity. In particular, compound C had a $EC_{50}$ at $6 \times 10^{-6}$.

Using the Virus Yield Method assessing activity against HSV-1 (KOS strain), compound B exhibited an $ID_{90}$ (uM) of 1.8 and Compound C exhibited an $ID_{90}$ of 2.8. In contrast, acyclovir (ACV), a known therapeutic agent for use in the treatment of HSV, exhibited an $ID_{90}$ (uM) against HSV-1 (KOS strain) of 14, approximately 7-fold higher than the preferred Compound C. In the Virus Yield method against HSV-2 (333), Compound B exhibited an $ID_{90}$ (uM) of 3 and Compound C exhibited an $ID_{90}$ (uM) of 2.

Using the Plaque Reduction Method, activity against HSV-1 KOS Phosphono formate resistant (PFAr) and KOS 9-(2-Phosphonylmethoxyethyl)-adenine resistant (PMEAr) strains was assessed. Against HSV-1 KOS (PFAr), Compound B exhibited an $ID_{50}$ (uM) of 1.4 and Compound C exhibited an $ID_{50}$ (uM) of 3.4. In contrast, acyclovir (ACV) exhibited an $ID_{50}$ (uM) of 6.2. Against HSV-1 KOS (PMEAr), Compound B exhibited an ID50 (uM) of 0.6 and Compound C exhibited an ID50 (uM) of 1.0.

Compounds B and C were tested for cytotoxicity against leukemia L1210 cells up to a concentration of $2 \times 10^{-3}$ according to the method described in Bobek and Bloch, J. Med. Chem., 20, 458, 1977. In addition, these compounds were tested for cytotoxicity against a human T-cell lymophoblast cell line (CEM) according to the method of Vazquez-Padua, et al., Cancer Comm., 2, 55–62 (1990) with the exception that the cell line was different, to assay the cells, the cells were counted with a cell counter and the cells were incubated for 4 days instead of for 3 days. In the L1210 assay, compound C evidenced virtually no cytotoxicity up to a concentration of $2 \times 10^{-3}$, whereas compound B evidenced significant cytotoxicity. In the CEM cytotoxicity experiment, Compound C evidenced an ID50 of more than 400 uM, which was significantly less toxic than Compound B.

Based upon the results of these experiments, 1-(2'-deoxy-B-D-ribofuranosyl)-5-ethyl-2-pyrazinone-4-N-oxide is a composition exhibiting exhanced anti-HSV activity (even against resistant strains) and very low cytotoxicity and is the preferred therapeutic agent for treatment of HSV.

Compound C also evidenced significant anti-EBV activity. In particular, when EBV DNA was assessed in a high EBV producer cell line (Hl, which is a subclone of P3HR-1 cells of Burkitt's lymphoma cell line), Compound C evidenced anti-EBV activity. The methodology employed in the EBV assay is similar to the method of Foster, et al., Jour. Biol. Chem., 266, 238, (1991), except that the EBV DNA was assessed with an EBV DNA probe BAMH IM.

Compound C also evidenced significant activity against Varicella Zoster (VZV) in the HLF human cell line. As tested, using the above-described methodology, 1uM of Compound C inhibited 90% of the Virus Yield.

Compound C was also examined against thymidine phosphorylase obtained from the human liver using standard methodology. Compound C was shown to be a substrate of the enzyme; however, the rate of breakdown by the enzyme is much less than the rate or breakdown of thymidine by that enzyme.

Utilizing the above-described procedure, other compositions according to the present invention are screened for antiHSV activity (I and II), including activity against resistant HSV strains, anti-EBV activty, anti-VZV activity and tested compounds exhibit activity.

It is to be understood by those skilled in the art that the foregoing description and examples are illustrative of practicing the present invention, but are in no way limiting. Variations of the detail presented herein may be made without departing from the spirit and scope of the present invention as defined by the following claims.

We claim:

1. A compound according to the structure:

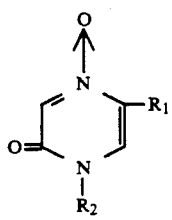

where
$R_1$ is H, $CH_3$, $C_2H_5$, $C_3H_7$, i-$C_3H_7$, $-CH_2-C_6H_5$, $-CH=CH_2$, $-CH=CH-CH_3$,

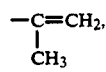

$-C\equiv CH$, $-C\equiv C-CH_3$, $-C\equiv C-C_6H_5$, I, Br, $CF_3$, $-CH=CHBr$, or $-CH=CH\ C_6H_5$;
$R_2$ is

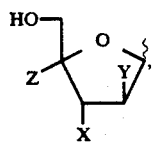

such that
X is H, OH, $CH_2OH$, $N_3$, $NH_2$, F, Cl or I, when Y is H, F or OH and Z is H or F;
Y is H, OH, $N_3$, $NH_2$, F, Br, Cl or I, when X is H, F or OH and Z is H or F;
Z is H, $CH_2OH$, F, Cl, I, $N_3$ or $NH_2$, when X and Y are H, F or OH,
provided that $R_1$ is not H or $CH_3$ when Y=Z=H and X=OH;
$R_3$ is H, F, Br, Cl, I or OH; and
$R_4$ is H, $CH_2OH$, $CH_2N_3$, $CH_2NH_2$, OH, F, Br, Cl or I.

2. The compound according to claim 1 wherein $R_1$ is $CH_3$, $C_2H_5$, I or $-CH=CHBr$.

3. The compound according to claim 1 where $R_2$ is

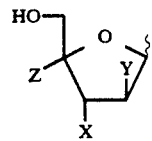

where X is H, OH, F or $N_3$ and Y and Z are H.

4. The compound according to claim 1 where X is OH, Y is OH or F and Z is H.

5. The compound according to claim 3 where Y and Z are H and X is $N_3$ or F.

6. The compound according to claim 3 where $R_1$ is $C_2H_5$ and Y and Z are H and X is OH.

7. The compound according to claim 3 where $R_1$ is H, $CH_3$, $C_2H_5$, $-CH=CH_2$ or $-CH=CHBr$.

8. The compound according to claim 2 where X, Y and Z are H.

9. The compound according to claim 3 where X is $N_3$.

10. The compound according to claim 1 where $R_2$ is

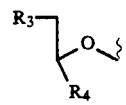

where $R_3$ is OH and $R_4$ is H.

11. The compound according to claim 10 where $R_1$ is H, $CH_3$, $C_2H_5$ or I.

12. The compound according to claim 3 where $R_1$ is $CH_3$ or $C_2H_5$ and Z is H, Y is H and X is OH.

13. A compound of the general structure:

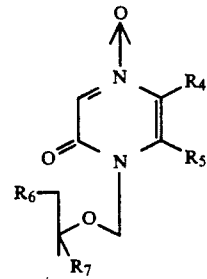

where
$R_4$ is H, $CH_3$, $C_2H_5$, $C_3H_7$, i-$C_3H_7$, $-CH_2-C_6H_5$, $-CH=CH_2$, $-CH=CH-CH_3$,

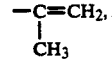

$-C\equiv CH$, $-C\equiv C-CH_3$, $-C\equiv C-C_6H_5$, I, Br, $CF_3$, $-CH=CHBr$, or $-CH=CH\ C_6H_5$;
$R_5$ is $S-C_6H_5$ or $-S-C_6H_{11}$;
$R_6$ is H, OH, F, Br, Cl, I, $N_3$ or $NH_2$; and
$R_7$ is H, OH, $N_3$, $NH_2$, $CH_2OH$, $CH_2N_3$, $CH_2NH_2$, F, Br, Cl or I.

14. The compound according to claim 13 where $R_6$ is OH and $R_7$ is H.

15. The compound according to claim 13 where $R_4$ is $CH_3$ or $C_2H_5$.

16. The compound according to claim 13 where $R_5$ is is $S-C_6H_5$.

17. A compound of the structure:

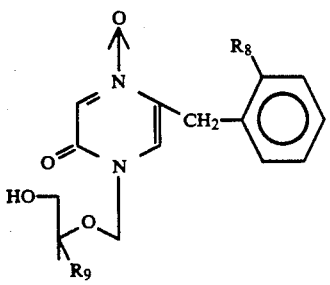

where R$_8$ is is H or —OCH$_2$C$_6$H$_5$; and
where R$_9$ is is H, CH$_2$OH, CH$_2$N$_3$, or CH$_2$NH$_2$.

18. The compound according to claim 17 where R$_8$ is O—CH$_2$C$_6$H$_5$.

19. The compound according to claim 17 where R$_9$ is H or CH$_2$OH.

20. The compound according to claim 17 where R$_8$ is O—CH$_2$C$_6$H$_5$ and R$_9$ is H.

21. A compound of the structure:

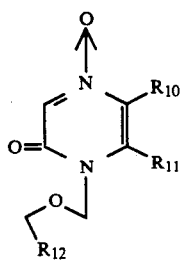

where
R$_{10}$ is —CH$_3$ or —CH$_2$CH$_3$;
R$_{11}$ is S—C$_6$H$_5$ or S—C$_6$H$_{11}$; and
R$_{12}$ is —C$_6$H$_5$ or —CH$_3$.

22. The compound according to claim 21 where R$_{10}$ is CH$_2$CH$_3$.

23. The compound according to claim 21 where R$_{11}$ is S—C$_6$H$_5$.

24. A pharmaceutical composition for treating cancer or viral infections in mammals, including humans, comprising a therapeutically effective amount of a compound having the structure:

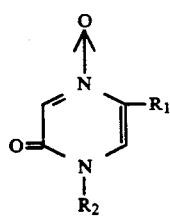

where
R$_1$ is H, CH$_3$, C$_2$H$_5$, C$_3$H$_7$, i-C$_3$H$_7$, —CH$_2$—C$_6$H$_5$, —CH=CH$_2$, —CH=CH—CH$_3$,

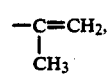

—C≡CH, —C≡C—CH$_3$, —C≡C—C$_6$H$_5$, I, Br, CF$_3$, —CH=CHBr, or —CH=CH C$_6$H$_5$;

R$_2$ is

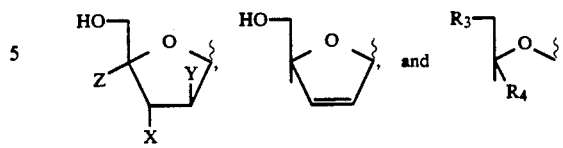

such that
X is H, OH, CH$_2$OH, N$_3$, NH$_2$, F, Cl or I, when Y is H, F or OH and Z is H or F;
Y is H, OH, N$_3$, NH$_2$, F, Br, Cl or I, when X is H, F or OH and Z is H or F;
Z is H, CH$_2$OH, F, Cl, I, N$_3$ or NH$_2$, when X and Y are H, F or OH,
provided that R$_1$ is not H or CH$_3$ when Y=Z=H and X=OH;
R$_3$ is H, F, Br, Cl, I or OH; and
R$_4$ is H, CH$_2$OH, CH$_2$N$_3$, CH$_2$NH$_2$, OH, F, Br, Cl or I.

25. The composition according to claim 24 wherein R$_1$ is CH$_3$, C$_2$H$_5$, I, —CH=CH$_2$ or —CH=CHBr.

26. The composition according to claim 24 where R$_2$ is

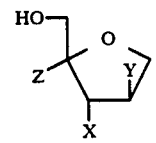

where X is H, OH, F or N$_3$ and Y and Z are H.

27. The composition according to claim 26 where R$_1$ is H, CH$_3$, C$_2$H$_5$, —CH=CH$_2$ or —CH=CHBr.

28. The composition according to claim 26 where X, Y and Z are H.

29. The composition according to claim 26 where X is N$_3$.

30. The composition according to claim 26 where R$_1$ is C$_2$H$_5$, Y and Z are H and X is OH.

31. The composition according to claim 24 where R$_2$ in said compound is

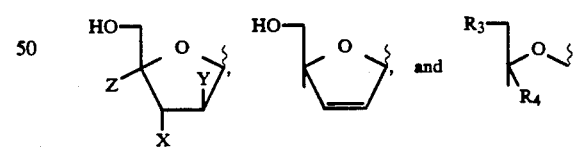

where R$_3$ is OH and R$_4$ is H.

32. The composition according to claim 31 where R$_1$ is H, CH$_3$, C$_2$H$_5$ or I.

33. The pharmaceutical composition according to claim 24 further comprising a pharmaceutically acceptable carrier or excipient.

34. The composition according to claim 33 adapted for parenteral, oral or topical administration.

35. A pharmaceutical composition for treating viral infections in mammals, including humans comprising a therapeutically effective amount of a compound having the general structure:

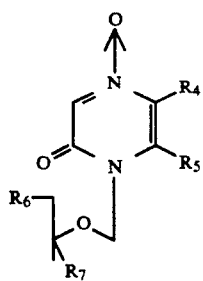

where
R$_4$ is H, CH$_3$, C$_2$H$_5$, C$_3$H$_7$, i-C$_3$H$_7$, —CH$_2$—C$_6$H$_5$, —CH=CH$_2$, —CH=CH-CH$_3$,

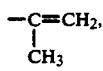

—C≡CH, —C≡C—CH$_3$, —C≡C—C$_6$H$_5$, I, Br, CF$_3$, —CH=CHBr, or —CH=CH C$_6$H$_5$;
R$_5$ is S—Ph or —S—C$_6$H$_{11}$;
R$_6$ is H, OH, F, Br, Cl, I, N$_3$ or NH$_2$; and
R$_7$ is H, OH, N$_3$, NH$_2$, CH$_2$OH, CH$_2$N$_3$, CH$_2$NH$_2$, F, Br, Cl or I.

36. The composition according to claim 35 where R$_6$ is OH and R$_7$ is H.

37. The composition according to claim 35 where R$_4$ is CH$_3$ or C$_2$H$_5$.

38. The composition according to claim 35 where R$_5$ is S-Ph.

39. The composition according to claim 35 further comprising a pharmaceutically acceptable carrier or excipient.

40. The composition according to claim 39 adapted for parenteral, oral or topical administration.

41. A pharmaceutical composition for treating viral infections in mammals, including humans comprising a therapeutically effective amount of a compound having the general structure:

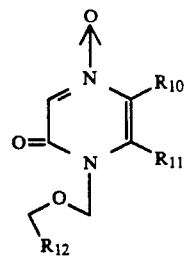

where
R$_{10}$ is —CH$_3$ or —CH$_2$CH$_3$;
R$_{11}$ is S—C$_6$H$_5$ or S—C$_6$H$_{11}$; and
R$_{12}$ is —C$_6$H$_5$ or —CH$_3$.

42. The composition according to claim 41 where R$_{10}$ is CH$_2$CH$_3$.

43. The composition according to claim 41 where R$_{11}$ is S—C$_6$H$_5$.

44. The composition according to claim 41 further comprising a pharmaceutically acceptable carrier or excipient.

45. A method of treating a patient suffering from a viral infection caused by at least one member of the herpes related disease group consisting of Herpes Simplex Virus I, Herpes Simplex Virus II, Epstein Barr Virus, Varicella Zoster and Cytomegalovirus comprising administering to said patient a therapeutically effective amount of a compound selected from the group consisting of 1-(2'-deoxyribofuranosyl)-5-methyl-2-pyrazinone-N-oxide and 1-(2'-deoxyribofuranosyl)-5-ethyl-2-pyrazinone-N-oxide.

46. The method according to claim 45 wherein said composition is 1-(2'-deoxyribofuranosyl)-5-ethyl-2-pyrazinone-N-oxide.

* * * * *